United States Patent
Norred et al.

(10) Patent No.: US 12,076,047 B2
(45) Date of Patent: Sep. 3, 2024

(54) UTERINE HEMORRHAGE CONTROLLING SYSTEM AND METHOD

(71) Applicant: Alydia Health, Inc., Menlo Park, CA (US)

(72) Inventors: Alexander James Norred, San Luis Obispo, CA (US); Davis Reed Carlin, Sammamish, WA (US); George Cochran Harper, Laguna Niguel, CA (US); David C. Lagrew, Jr., Irvine, CA (US); Amelia Michele Degenkolb, San Luis Obispo, CA (US)

(73) Assignee: Alydia Health, Inc., Menlo Park, CA (US)

( * ) Notice: Subject to any disclaimer, the term of this patent is extended or adjusted under 35 U.S.C. 154(b) by 60 days.

(21) Appl. No.: 16/938,769

(22) Filed: Jul. 24, 2020

(65) Prior Publication Data
US 2020/0352602 A1    Nov. 12, 2020

Related U.S. Application Data

(63) Continuation-in-part of application No. 16/367,068, filed on Mar. 27, 2019, now Pat. No. 11,241,254,
(Continued)

(51) Int. Cl.
*A61B 17/42*    (2006.01)
*A61B 17/12*    (2006.01)
(Continued)

(52) U.S. Cl.
CPC ............. *A61B 17/42* (2013.01); *A61M 1/916* (2021.05); *A61B 17/1204* (2013.01);
(Continued)

(58) Field of Classification Search
CPC ....................................................... A61B 17/42
See application file for complete search history.

(56) References Cited

U.S. PATENT DOCUMENTS

| 1,928,992 | A | 10/1933 | Clark et al. |
| 2,185,927 | A | 1/1940 | Shelanski |

(Continued)

FOREIGN PATENT DOCUMENTS

| CN | 2097618 U | 3/1992 |
| CN | 2116469 U | 9/1992 |

(Continued)

OTHER PUBLICATIONS

Balloon Uterine Stent, Cook Medical, Cook, 2017, 3 pages, [Online] [Retrieved on Dec. 21, 2017] Retrieved from the Internet <URL:https://www.cookmedical.com/products/wh_bus_webds/>.

(Continued)

*Primary Examiner* — Susan S Su
*Assistant Examiner* — Meagan Ngo
(74) *Attorney, Agent, or Firm* — Jordan IP Law, LLC

(57) ABSTRACT

A method of reducing postpartum bleeding includes positioning a device comprising a vacuum element within the uterus; sealing the uterus; activating vacuum in the uterus with the vacuum element of the device while the uterus is sealed; and collapsing the uterus with the vacuum to reduce postpartum bleeding.

18 Claims, 14 Drawing Sheets

Related U.S. Application Data which is a continuation of application No. 16/035,543, filed on Jul. 13, 2018, now Pat. No. 11,291,473, which is a continuation of application No. 13/827,579, filed on Mar. 14, 2013, now Pat. No. 10,064,651, which is a continuation-in-part of application No. 13/420,871, filed on Mar. 15, 2012, now Pat. No. 9,550,014.

(60) Provisional application No. 62/878,255, filed on Jul. 24, 2019.

(51) Int. Cl.
*A61B 17/30* (2006.01)
*A61M 1/00* (2006.01)

(52) U.S. Cl.
CPC ... *A61B 17/12136* (2013.01); *A61B 2017/306* (2013.01); *A61B 2217/005* (2013.01)

(56) References Cited

U.S. PATENT DOCUMENTS

| | | | |
|---|---|---|---|
| 2,286,462 A | 6/1942 | Chaffin | |
| 2,400,251 A | 5/1946 | Nagel | |
| 2,483,851 A | 10/1949 | Smith | |
| 2,925,904 A | 2/1960 | Eichholz | |
| 2,981,255 A | 4/1961 | Heyns | |
| 3,062,215 A | 11/1962 | Heyns | |
| 3,517,665 A | 6/1970 | Sheldon | |
| 3,626,928 A | 12/1971 | Barringer et al. | |
| 3,670,732 A | 6/1972 | Robinson | |
| 3,774,613 A | 11/1973 | Woods, Jr. et al. | |
| 3,828,781 A | 8/1974 | Rothman | |
| 3,835,843 A | 9/1974 | Karman | |
| 3,848,602 A | 11/1974 | Gutnick | |
| 3,923,051 A | 12/1975 | Soichet | |
| 3,929,133 A | 12/1975 | Ragab | |
| 4,013,079 A | 3/1977 | Lindemann et al. | |
| 4,111,209 A | 9/1978 | Wolvek et al. | |
| 4,141,360 A | 2/1979 | Lasswell | |
| 4,444,548 A | 4/1984 | Andersen et al. | |
| 4,533,345 A | 8/1985 | Louw | |
| 4,552,557 A | 11/1985 | Rangaswamy | |
| 4,563,183 A | 1/1986 | Barrodale et al. | |
| 4,681,123 A | 7/1987 | Valtchev | |
| 4,767,404 A | 8/1988 | Renton | |
| 4,784,654 A | 11/1988 | Beecher | |
| 4,807,625 A | 2/1989 | Singleton | |
| 4,925,452 A | 5/1990 | Melinyshyn et al. | |
| 4,955,875 A | 9/1990 | Knowles | |
| 4,981,477 A | 1/1991 | Schon et al. | |
| 5,030,202 A | 7/1991 | Harris | |
| 5,100,395 A | 3/1992 | Rosenberg | |
| 5,104,377 A | 4/1992 | Levine | |
| 5,160,325 A | 11/1992 | Nichols et al. | |
| 5,242,438 A | 9/1993 | Saadatmanesh et al. | |
| 5,254,084 A | 10/1993 | Geary | |
| 5,360,414 A | 11/1994 | Yarger | |
| 5,431,173 A | 7/1995 | Chin et al. | |
| 5,451,208 A | 9/1995 | Goldrath | |
| 5,464,409 A | 11/1995 | Mohajer | |
| 5,472,435 A * | 12/1995 | Sutton | A61M 27/00 604/540 |
| 5,569,284 A | 10/1996 | Young et al. | |
| 5,603,685 A | 2/1997 | Tutrone, Jr. | |
| 5,769,880 A * | 6/1998 | Truckai | A61M 16/0481 607/101 |
| 5,800,414 A | 9/1998 | Cazal | |
| 5,807,282 A | 9/1998 | Fowler | |
| 5,928,249 A * | 7/1999 | Saadat | A61B 17/42 606/119 |
| 5,941,873 A | 8/1999 | Korenfeld | |
| 6,350,463 B1 | 2/2002 | Herman et al. | |
| 6,443,947 B1 | 9/2002 | Marko et al. | |
| 6,506,149 B2 | 1/2003 | Peng et al. | |
| 6,508,815 B1 | 1/2003 | Strul et al. | |
| 6,641,575 B1 * | 11/2003 | Lonky | A61B 17/0218 600/210 |
| 6,676,680 B1 | 1/2004 | Packer | |
| 6,736,822 B2 | 5/2004 | McClellan et al. | |
| 7,247,141 B2 | 7/2007 | Makin et al. | |
| 7,325,546 B2 | 2/2008 | Burbank et al. | |
| 7,512,445 B2 | 3/2009 | Truckai et al. | |
| 7,708,716 B2 | 5/2010 | Shah | |
| 8,197,470 B2 | 6/2012 | Sharkey et al. | |
| 8,221,401 B2 | 7/2012 | Sharkey et al. | |
| 8,287,552 B2 | 10/2012 | Grillo | |
| 9,125,686 B2 | 9/2015 | Norred et al. | |
| 9,301,770 B2 | 4/2016 | Gruber | |
| 9,550,014 B2 | 1/2017 | Norred et al. | |
| 9,763,731 B2 | 9/2017 | Dubois et al. | |
| 9,919,083 B2 | 3/2018 | Blin | |
| 10,064,651 B2 | 9/2018 | Norred et al. | |
| 2002/0010457 A1 | 1/2002 | Duchon et al. | |
| 2003/0064746 A1 | 4/2003 | Rader et al. | |
| 2003/0191452 A1 | 10/2003 | Meglin et al. | |
| 2004/0006331 A1 | 1/2004 | Shchervinsky | |
| 2004/0122352 A1 | 6/2004 | John | |
| 2004/0220550 A1 | 11/2004 | Schryver | |
| 2005/0085880 A1 * | 4/2005 | Truckai | A61B 90/04 607/101 |
| 2005/0113852 A1 * | 5/2005 | Burbank | A61B 17/42 606/158 |
| 2005/0261663 A1 | 11/2005 | Patterson et al. | |
| 2007/0032814 A1 | 2/2007 | Hibler | |
| 2007/0149998 A1 | 6/2007 | Wicks et al. | |
| 2008/0045924 A1 | 2/2008 | Cox et al. | |
| 2008/0051708 A1 | 2/2008 | Kumar et al. | |
| 2008/0188863 A1 * | 8/2008 | Chu | A61B 17/12 606/119 |
| 2008/0319472 A1 | 12/2008 | Shelley | |
| 2009/0048685 A1 | 2/2009 | Frigstad et al. | |
| 2009/0093795 A1 | 4/2009 | Koeper | |
| 2010/0069886 A1 | 3/2010 | Wilkes | |
| 2010/0191279 A1 | 7/2010 | Kassab et al. | |
| 2010/0198214 A1 | 8/2010 | Layton et al. | |
| 2010/0228239 A1 | 9/2010 | Freed | |
| 2010/0274260 A1 * | 10/2010 | D'Arpiany | A61B 17/4241 606/119 |
| 2011/0087337 A1 | 4/2011 | Forsell | |
| 2011/0098524 A1 | 4/2011 | Barcelo Rojas | |
| 2011/0208178 A1 | 8/2011 | Truckai | |
| 2012/0041419 A1 | 2/2012 | Blanchard et al. | |
| 2012/0071841 A1 | 3/2012 | Bengtson | |
| 2012/0172889 A1 | 7/2012 | Chin et al. | |
| 2013/0266165 A1 | 10/2013 | Neumeyer | |
| 2013/0296816 A1 | 11/2013 | Greener | |
| 2014/0079241 A1 | 3/2014 | Chan et al. | |
| 2014/0163532 A1 | 6/2014 | Cornet et al. | |
| 2014/0200591 A1 | 7/2014 | Sullivan et al. | |
| 2014/0228801 A1 | 8/2014 | Keeling | |
| 2014/0228877 A1 | 8/2014 | Kassab et al. | |
| 2015/0080861 A1 | 3/2015 | Ozer | |
| 2015/0142032 A1 | 5/2015 | Scheib et al. | |
| 2015/0165151 A1 | 6/2015 | Payton et al. | |
| 2017/0035949 A1 | 2/2017 | Loske | |
| 2017/0281231 A1 | 10/2017 | Langell et al. | |
| 2018/0055523 A1 | 3/2018 | Bair et al. | |
| 2019/0083132 A1 | 3/2019 | Norred et al. | |
| 2019/0216504 A1 | 7/2019 | Norred et al. | |

FOREIGN PATENT DOCUMENTS

| | | |
|---|---|---|
| CN | 2149183 Y | 12/1993 |
| CN | 2254720 Y | 5/1997 |
| CN | 2415733 Y | 1/2001 |
| CN | 2464264 Y | 12/2001 |
| CN | 2467062 Y | 12/2001 |
| CN | 2559321 Y | 7/2003 |
| CN | 2565407 Y | 8/2003 |
| CN | 2633227 Y | 8/2004 |
| CN | 2662850 Y | 12/2004 |

(56) References Cited

FOREIGN PATENT DOCUMENTS

| | | |
|---|---|---|
| CN | 2933317 Y | 8/2007 |
| CN | 201185945 Y | 1/2009 |
| CN | 101366650 A | 2/2009 |
| CN | 201337472 Y | 11/2009 |
| CN | 201356633 Y | 12/2009 |
| CN | 201361088 Y | 12/2009 |
| CN | 202044560 U | 11/2011 |
| CN | 202146327 U | 2/2012 |
| CN | 202288422 U | 7/2012 |
| CN | 203122506 U | 8/2013 |
| CN | 106390212 A | 2/2017 |
| CN | 106821472 A | 6/2017 |
| CN | 206587003 U | 10/2017 |
| CN | 107427659 A | 12/2017 |
| CN | 206852626 U | 1/2018 |
| CN | 207220865 U | 4/2018 |
| GB | 839965 A | 6/1960 |
| GB | 1469584 A | 4/1977 |
| IN | 200300065 I3 | 1/2005 |
| IN | 5953CHE2014 | 2/2015 |
| IN | 4745CHE2015 | 8/2016 |
| JP | 2001513357 A | 9/2001 |
| JP | 2007523716 A | 8/2007 |
| KR | 20010002164 A | 1/2001 |
| RU | 2113246 C1 | 6/1998 |
| RU | 98112 U1 | 10/2010 |
| RU | 102509 U1 | 3/2011 |
| RU | 2429792 C1 | 9/2011 |
| RU | 2440038 C2 | 1/2012 |
| SU | 1426560 A1 | 9/1988 |
| SU | 1431746 A1 | 10/1988 |
| WO | WO2001/080788 A2 | 11/2001 |
| WO | WO2011/097350 A1 | 8/2011 |
| WO | WO2012/137894 A1 | 10/2012 |
| WO | WO2020/123525 A1 | 6/2020 |

OTHER PUBLICATIONS

Ebb—Clinical Innovations—forMOM. forBABY. forLIFE, Clinical Innovations, LLC, 2016, 6 pages, [Online] [Retrieved on Dec. 21, 2017] Retrieved from the Internet <URL:http://clinicalinnovations.com/portfolio-items/ebb/>.

Ebb, Complete Tamponade System, Clinical Innovations, LLC, undated, 2 pages, [Online] [Retrieved on Dec. 21, 2017] Retrieved from the Internet <URL: http://clinicalinnovations.com/wp-content/uploads/2017/04/056-0086-Rev.-B.pdf>.

Hofmeyr, J.; Uterine suction devices: Review of literature and potential role; Effective care research unit, Univ. of the Witwatersrand/Fort Hare/Eastern Cape Dept. of Health; 22 pages; known of at least by Nov. 2018.

Manage Postpartum Hemorrhage, Bakri, Postpartum Balloon With Rapid Instillation Components, Cook, Mar. 2017, 4 pages, [Online] [Retrieved on Dec. 21, 2017] Retrieved from the Internet <URL: https://www.cookmedical.com/data/resources/RH-D28438-EN-F_M3_1489434681697.pdf>.

Panicker, T.N.V., "Panicker's Vacuum Suction Haemostatic Device for Treating Post-Partum Haemorrhage," The Journal of Obstetrics and Gynecology of India, Mar.-Apr. 2017, pp. 150-151, vol. 67, No. 2, [Online] [Retrieved on Mar. 26, 2018] Retrieved from the Internet <URL:http://www.jogi.co.in/march_april_17/pdf/14_iat.pdf>.

Goates, T. et al.; Poster: UVAC Uterine Vacuum Assisted Contraction, University of Utah Health Science, Center for Medical Innovation, Bench to Bedside, Apr. 2016.

Postpartum Hemorrhage PPH Bakri Style Balloon BT—Cath Balloon Tamponade Catheter, Utah Medical Products Inc., 1999-2017, 3 pages, [Online] Retrieved from the Internet <URL: http://www.utahmed.com/bt-cath.html>.

Purwosunu et al.; Control of postpartum hemorrhage using vacuum-induced uterine tamponade; Obstetrics and Gynecology: 128(1); pp. 33-36; Jul. 2016.

Ram, S. et al., "Vacuum Retraction of Uterus for the Management of Atonic Postpartum Hemorrhage," IOSR Journal of Dental and Medical Sciences (IOSR-JDMS), Nov. 2014, pp. 15-19, vol. 13, Issue 11, Ver. III. May be Retrieved at <URL: https://www.researchgate.net/publication/284005732_Vacuum_retraction_of_ute rus_for_the_management_of_atonic_postpartum_hemorrhage>.

Shields et al.; ACOG Practice Bulletin—Clinical Management Guidelines for Obstetrician-Gynecologists; Postpartum Hemorrhage; Obstetrics and Gynecology; 130(4); pp. e168-e186; Oct. 2017.

Video of B2B Competition 2016, Bench 2 Bedside Student Program; Can be Viewed at <URL: http://uofuhealth.utah.edu/center-for-medical-innovation/backup_folder/index-old.php>. [PDF of program contents enclosed].

Dr. Panicker's PPH Suction Device—INSTASTOP; (Screenshot) 1 page; retrieved from the internet at YouTube (https://www.youtube.com/watch?v=a-QlpkeT3Gg); Published Jan. 26, 2017.

Panickers PPH Suction Device; (Screenshot) 1 page; retrieved from the internet at YouTube (https://www.youtube.com/watch?v=KDa_tl_p3qVM); Published Apr. 9, 2015.

Panicker's PPH Suction Device; (Screenshot) 1 page; retrieved from the internet at YouTube (https://www.youtube.com/watch?v=uQYoWEbWJOg); Published Oct. 25, 2016.

Webinar on: Vacuum Retraction Cannula for Managing Atonic PPH; (Screenshot) 1 page; retrieved from the internet at YouTube (https://www.youtube.com/watch?v=FSpn8JLSQIA); Published Oct. 25, 2016.

* cited by examiner

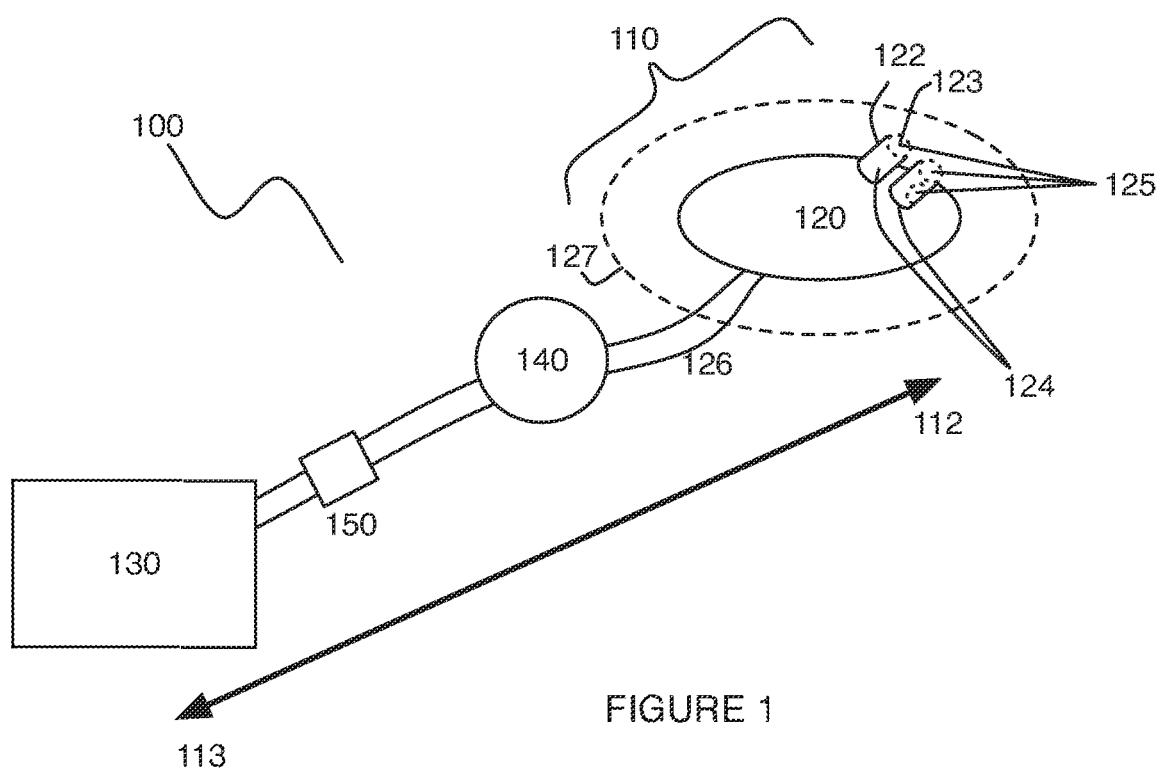
FIGURE 1
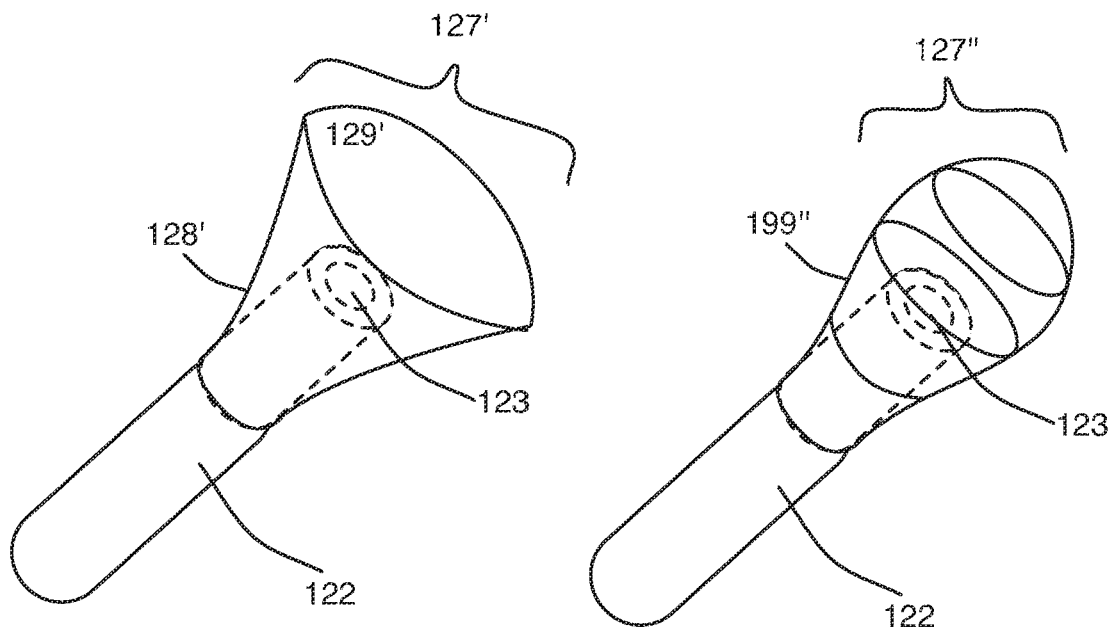
FIGURE 2A
FIGURE 2B

UTERINE HEMORRHAGE CONTROLLING SYSTEM AND METHOD

CROSS-REFERENCE TO RELATED APPLICATIONS

This application claims priority to U.S. Patent Provisional Application No. 62/878,255, filed on Jul. 24, 2019, and titled "UTERINE HEMORRHAGE CONTROLLING SYSTEM AND METHOD," the entirety of which is incorporated by reference herein.

This application is a continuation-in-part of U.S. patent application Ser. No. 16/367,068, filed on Mar. 27, 2019, titled "UTERINE HEMORRHAGE CONTROLLING SYSTEM AND METHOD," now U.S. Patent Publication No. US-2019-0216504-A1, which is a continuation of U.S. patent application Ser. No. 16/035,543, filed Jul. 13, 2018, and titled "UTERINE HEMORRHAGE CONTROLLING SYSTEM AND METHOD," now U.S. Patent Publication No. US-2019-0083132-A1, which is a continuation of U.S. patent application Ser. No. 13/827,579, filed Mar. 14, 2013, and titled "UTERINE HEMORRHAGE CONTROLLING SYSTEM AND METHOD," now U.S. Pat. No. 10,064,651, which is a continuation-in-part of U.S. patent application Ser. No. 13/420,871, filed Mar. 15, 2012, titled "POSTPARTUM UTERINE CONTRACTILE APPARATUS AND METHOD," now U.S. Pat. No. 9,550,014, each of which is incorporated herein by reference in its entirety for all purposes.

This application may also be related to International Patent Application No. PCT/U2019/065504, filed on Dec. 10, 2019, titled "POSTPARTUM UTERINE HEMORRHAGE DEVICE," now PCT Publication No. 2020/123525, the entirety of which is incorporated by reference herein.

TECHNICAL FIELD

This invention relates generally to the medical device field, and more specifically to an improved uterine hemorrhage controlling system and method.

BACKGROUND

Postpartum uterine bleeding can occur when the uterine muscles are unable to achieve adequate contraction after delivery to cut off the blood flow that formerly circulated in the utero-placental space to nourish the unborn child(ren). The condition for this lack of contraction is called atony (lack of tone). The mechanism by which the contraction of the uterine muscles typically cuts off the blood flow is by a cross-hatch configuration of the myometrium whereby contraction of the muscles of the cross-hatch configuration effectively pinch the arterial vessels that run through the cross-hatch sections. In some cases, atony can result in arterial vessels that continue to bleed into the uterus (i.e., postpartum uterine bleeding). The rate of bleeding can vary from a trickle to what is described as faucet flow, which can have a flow rate similar to the placental flow to the fetus at full term (approximately 750 ml/min).

Postpartum hemorrhage, or excessive uterine blood loss after birth, is the leading cause of maternal death in the world, claiming the lives of over 125,000 mothers every year. Inability to control postpartum bleeding can require a woman to receive multiple blood transfusions, and in severe cases, a full hysterectomy. Accordingly, it is desirable to control such postpartum bleeding, if possible, at its onset.

The cause of postpartum hemorrhage, in approximately 80% of cases, is uterine atony, which is the inability of the woman's uterus to contract after delivering the child. Risk factors for uterine atony include prolonged stage of labor, preeclampsia, and multiparity.

Postpartum hemorrhage has been traditionally treated using oxytoxic agents, hormonal agents that induce muscle contraction. Unfortunately, studies have increasingly shown that oxytoxic agents do not significantly reduce either the incidence of postpartum hemorrhage or the amount of blood lost. Some studies have even indicated that oxytoxic agents are being overused to the point that this treatment increases the risk of uterine atony. Current medical devices and surgical procedures have also proven inadequate in reducing postpartum hemorrhage or the amount of blood lost, and/or are extremely invasive.

It has recently been discovered by the inventors that providing negative pressure (i.e., vacuum) within the uterus, in combination with sealing an opening to the uterus or vagina at the distal end, can rapidly induce uterine contraction to counteract uterine atony, thus reducing or entirely stopping uterine hemorrhaging. Providing negative pressure may furthermore be performed in a non-invasive (i.e., non-surgical) manner, effectively removing an inadequacy of other hemorrhage-controlling options. With the knowledge of this discovery, the inventors have created an improved uterine hemorrhage controlling system and method.

SUMMARY OF THE DISCLOSURE

In general, in one embodiment, a method of reducing postpartum bleeding includes positioning a device having a vacuum element at least partially within the uterus, sealing the uterus, activating vacuum in the uterus with the vacuum element of the device while the uterus is sealed, and collapsing the uterus with the vacuum to reduce postpartum bleeding.

This and other embodiments can include one or more of the following features. Positioning the device can include transvaginally delivering the vacuum element to the uterus. The method can further include reversibly deforming the vacuum element prior to positioning the device within the uterus. The vacuum element can include a plurality of openings. Activating vacuum can include activating vacuum through the plurality of openings. Collapsing the uterus can include collapsing tissue onto a shield of the device so as to prevent obstruction of the plurality of openings. The vacuum element can be curved. The plurality of openings can be positioned along an inner circumference of the curved vacuum element. Sealing the uterus can include placing the seal at the vulva, cervix, or vaginal canal. Sealing the uterus can include expanding a seal against tissue proximate to or within the uterus. Expanding the seal can include delivering fluid to an interior of the seal. Activating vacuum can include activating vacuum with a vacuum pump connected to the vacuum element. Activating vacuum can include producing a negative pressure within the uterus of up to 3 psi. The method can further include removing fluid from the uterus after activating vacuum. Activating vacuum can counteract uterine atony. Activating vacuum can facilitate closing of exposed uterine arterioles in a wall of the uterus. The method can further include maintaining vacuum until hemorrhaging has substantially stopped. The method can further include maintaining vacuum for 1-24 hours. The method can further include monitoring a flow of blood out of the uterus while vacuum is activated. Monitoring the flow of blood can include monitoring through a transparent portion of the device.

In general, in one embodiment, a method of reducing postpartum bleeding includes positioning a device having a vacuum element at least partially within a uterus, sealing the uterus with a seal of the device, activating vacuum in the uterus with the vacuum element of the device while the uterus is sealed, and collapsing endometrial trumpet-shaped arteries at an inner surface of the uterus with the vacuum to reduce postpartum bleeding.

This and other embodiments can include one or more of the following features. The method can further include collapsing the uterus with the vacuum to cause contraction of uterine muscles and reduce postpartum bleeding. Activating vacuum can include supplying vacuum from a pump at between 1 L/min and 20 L/min. Activating vacuum can include supplying vacuum from a pump at between 10 L/min and 15 L/min. Activating vacuum can include producing a pressure of 40-160 mmHg. Activating vacuum can include producing a pressure of 50-100 mmHg. Activating vacuum can include producing a pressure of 70-90 mmHg. Sealing the uterus can include placing the seal in the lower uterus, cervix, vaginal canal, or at the vulva. Sealing the uterus can include sealing so as to hinder a flow of air into the uterus while vacuum is applied in order to achieve a therapeutic isobaric level of vacuum throughout the uterus. The method can further include maintaining an isobaric condition within the uterus after activating vacuum. Activating vacuum can include activating with a pump having a vacuum reservoir therein so as to enable a consistent flow of vacuum to the uterus. The method can further include detecting air in a tube connected to the vacuum element to determine if there is a leak in a seal. The method can further include visualizing a flow of blood from the uterus through a translucent or transparent tube connected to the vacuum element. The steps of positioning, sealing, activating, and collapsing can result in stopping postpartum bleeding within 5 hours. The steps of positioning, sealing, activating, and collapsing can result in stopping postpartum bleeding within 2 hours. The method can further include confirming that a cervix is dilated to greater than 3 cm prior to the positioning step. A leak rate past the seal can be less than a pump rate of a pump supplying the vacuum.

In general, in one embodiment, a method of reducing postpartum bleeding includes positioning a device comprising a vacuum element at least partially within a uterus, sealing the uterus with a seal of the device, activating vacuum in the uterus with the vacuum element of the device while the uterus is sealed, collapsing the uterus with the vacuum, and maintaining an isobaric condition within the uterus after activating vacuum to reduce postpartum bleeding.

In general, in one embodiment, a system configured to treat postpartum hemorrhaging includes a suction module and a pump system. The suction module includes a vacuum element and a sealing portion. The vacuum element is configured to be placed within a uterus and includes a plurality of holes therein. The sealing portion is connected to the vacuum element and has a seal configured to seal the uterus. The pump system is configured to connect to the suction module so as to activate vacuum in the uterus through the vacuum element. The pump system includes a pump, a vacuum reservoir, and a pressure regulator configured to regulate a pressure between the vacuum reservoir and the suction module so as to maintain a substantially constant vacuum within the uterus.

This and other embodiments can include one or more of the following features. The pump can be an intermittent pump. The pump can be a manual pump. The pump can be configured to draw a vacuum that is higher than a vacuum through the suction module. The pump system can further include a pressure gauge connected to the vacuum reservoir and configured to indicate a pressure in the vacuum reservoir. The pump system can further include a separation canister configured to prevent fluids from reaching the pressure regulator.

In general, in one embodiment, a system configured to treat postpartum hemorrhaging includes a suction module and a connecting tube. The suction module includes a vacuum element and a sealing portion. The vacuum element is configured to be placed within a uterus and includes a plurality of holes therein. The sealing portion is connected to the vacuum element and has a seal configured to seal the uterus. The connecting tube is connected to the suction module and is configured to connect to a vacuum pump to as to activate vacuum in the uterus through the vacuum element. The connecting tube is transparent or translucent so as to enable viewing of a flow of blood therethrough.

In general, in one embodiment, a system configured to treat postpartum hemorrhaging includes a suction module and a connecting tube. The suction module includes a vacuum element and a sealing portion. The vacuum element is configured to be placed within a uterus and includes a plurality of holes therein. The sealing portion is connected to the vacuum element and has a seal configured to seal the uterus. The connecting tube is connected to the suction module and is configured to connect to a vacuum pump to as to activate vacuum in the uterus through the vacuum element. The vacuum is configured to collapse endometrial trumpet-shaped arteries at an inner surface of the uterus to reduce postpartum bleeding.

Any of these embodiments can include one or more of the following. The vacuum can be configured to collapse the uterus to cause contraction of uterine muscles and reduce postpartum bleeding. The seal can be configured to be positioned in the lower uterus, cervix, vaginal canal, or at the vulva. The vacuum element can be looped. The plurality of holes can be positioned along an interior surface of the looped vacuum element. The system can further include a shield coupled to and extending along the vacuum element. The vacuum element can be atraumatic. The seal can be configured to expand from a collapsed configuration to an expanded configuration.

BRIEF DESCRIPTION OF THE FIGURES

FIG. 1 depicts an embodiment of a uterine hemorrhage controlling system;

FIGS. 2A-2C depict variations of a suction tube and shield of an embodiment of a uterine hemorrhage controlling system;

DESCRIPTION OF THE PREFERRED EMBODIMENTS

Figure 2C:
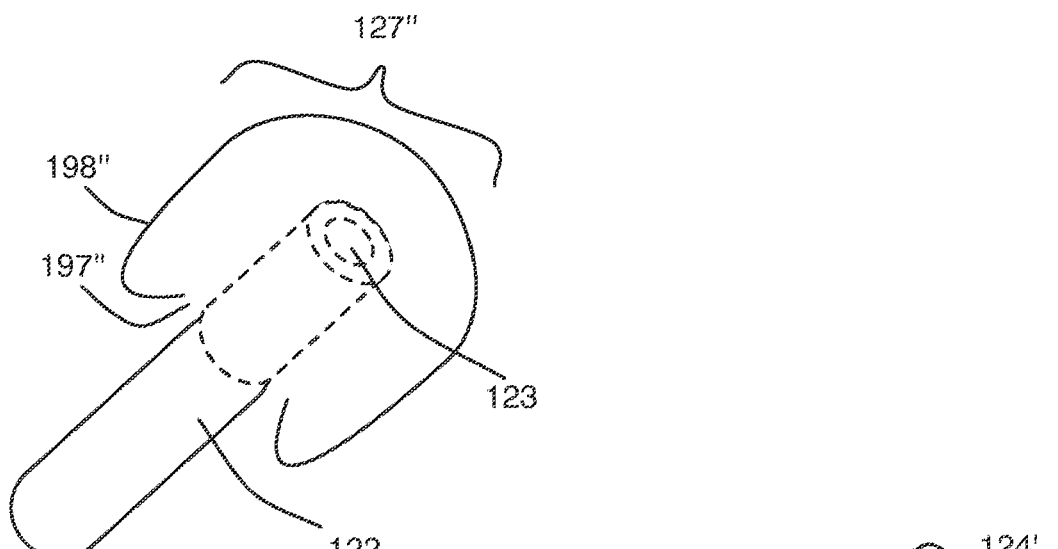

The following description of preferred embodiments of the invention is not intended to limit the invention to these preferred embodiments, but rather to enable any person skilled in the art to make and use this invention.

1. System

As shown in FIG. 1, an embodiment of a uterine hemorrhage controlling system 100 comprises a suction module 110 including a suction end 120 coupleable to a pump 130 by a connecting tube 126, and a sealing module 140 coupled to the suction module 110. The system 100 may further comprise the pump 130 and a filter 150 coupled to the suction module 110. At least a portion of the system 100 is preferably delivered transvaginally, and facilitates contraction of the uterus to counteract uterine atony. Thus, the system 100 functions to reduce or entirely stop uterine hemorrhaging, in order to substantially reduce total blood lost from the uterus after childbirth. The system 100 may further function to reduce other issues associated with childbirth, including a need for a blood transfusion or a hysterectomy.

1.1 System—Suction Module

The suction module 110 comprises a suction end 120 coupleable to a pump 130 by a connecting tube 126, and functions to provide negative pressure (i.e., vacuum) within the uterus to facilitate uterine contraction. Preferably, negative pressure provided by the suction module 110 results in a uniform mechanical stimulus to the uterine wall, in order to facilitate substantially even contractile movement of tissue; however, the suction module 110 may alternatively be configured to provide a non-uniform mechanical stimulus to the uterine wall, or to decrease intra-uterine pressure and/or volume by any suitable method (e.g., mechanically, chemically, creation of a vacuum, reduction in intrauterine temperature). The suction module 110 preferably comprises a distal end 112 and a proximal end 113, as shown in FIG. 1, wherein the distal end 112 comprises the suction end 120 and is configured to enter the uterus, and the proximal end 113 comprises the pump 130 and is configured to remain external to the uterus. However, both the distal end 112 and the proximal end 113 may be configured to enter the uterus. Preferably, the distal end 112 and the proximal end 113 are coupled by the connecting tube 126 (e.g., by a conduit, tubing, chamber), and may be further configured to be reversibly coupled in variations wherein at least one of the distal end 112 and the proximal end 113 is configured to be disposable. In some variations, the suction module 110 may further comprise a pressure sensor and/or a controller, which functions to facilitate measurement of a pressure provided by the pump 130 and/or a pressure within the uterus, and also to controllably adjust a negative pressure provided within the uterus.

The suction end 120 is configured to be transvaginally delivered, and functions to transmit a negative pressure provided by the pump 130 to the interior of the uterus, while preventing tissue or any other substance within the uterus from obstructing the suction end 120. The suction end 120 is preferably flexible, and may be further configured to be deformed into one or more configurations. Flexibility in the suction end 120 may further function to facilitate conformation of the suction end 120 to the intra-uterine anatomy of the patient. Variations of a flexible suction end 120 may be configured to be reversibly or irreversibly deformable. Alternatively, the suction end 120 may be rigid and substantially non-deformable, or may be configured to be rigid in one environment, and transition to a flexible state in another environment. Preferably, the suction end 120 is composed or partially composed of a medical-grade material (e.g., polyethylene, polypropylene, stainless steel, cobalt chrome, ceramic), such that the suction end 120 does not induce an adverse reaction after being inserted into a uterus of the patient. The suction end 120 may further be configured to prevent or counteract an inflammatory or biorejection response by processing the suction end material with anti-inflammatory and/or anti-biorejection agents (e.g., steroidal or non-steroidal anti-inflammatory agents). However, the suction end 120 may alternatively be composed of any suitable material that does not prevent the suction end 120 from transmitting a negative pressure to the interior of the uterus.

Preferably, at least a portion of the suction end 120 is configured to be disposable, such that the suction module 110 is modular and comprises components that may be removably attached together. In variations of a modular suction module 110, attachment locations between various components are preferably configured to provide hermetic seals, in order to prevent fluid and/or air leakage along the suction module 110. At least a portion of the suction end 120 may alternatively be configured to be reusable, and may or may not comprise hermetic seals at locations of coupling. In variations wherein a portion of the suction end 120 is configured to be reusable, the suction end 120 preferably comprises a material that may be sterilized without compromising the function of the suction end 120. The material may be configured to be sterilized by dry heat sterilization, moist heat sterilization, ethylene oxide sterilization, radiation (e.g., ultraviolet, gamma, electron beam), liquid chemical sterilization, or any other suitable sterilization method. In a specific example, the material is configured to be sterilized according to the U.S. Food and Drug Administration 510(k) Sterility Review Guidance K90-1.

The suction end 120 of the preferred embodiments includes a suction tube 122 and a shield 127 coupled to a distal portion of the suction tube 122 configured to enter the uterus. The suction end 120 may, however, omit the shield 127 in other embodiments. The suction tube 122 comprises an opening 123 fluidically coupled to a lumen of the connecting tube 126, which functions to allow a negative pressure to be transmitted from the pump 130, through the connecting tube 126, to the uterus. Preferably, the suction tube 122 is flexible, as described above; however, the suction tube 122 may alternatively be non-flexible or undergo a transition from a flexible state to a rigid state in different environments. Additionally, the suction tube 122 may be one of a set of suction tubes 124 coupled to the pump 130, such that the suction end 120 has an inherent redundancy of suction tubes configured to allow a negative pressure to be transmitted into the uterus.

Furthermore, the suction tube(s) may comprise a set or plurality of openings 125, the suction tube(s) may be configured to have a curved portion, and/or the suction tube(s) may be configured to have a non-curved portion. Having a plurality of openings 125 may, in some embodiments, provide redundancy such that even if some openings 125 become plugged with tissue or body fluids, vacuum will still permeate into and throughout the uterus through the remaining or unplugged openings 125 during use of the system 100.

Additionally, the suction tube(s) 122 may have any suitable length, diameter, or cross-sectional shape (e.g., uniform, non-uniform) configured to facilitate provision of a negative pressure within the uterus.

In a first variation, the suction end 120 comprises a single suction tube 122 with a single opening 123. In an example of the first variation, a lumen of the single suction tube 122 terminates in the single opening 123 at a distal end of the suction tube 122, and in another example of the first variation, the single opening 123 is located at any point along the length of the suction tube 122. In a second variation, the suction end 120 comprises a single suction tube 122 with a set of openings 125. In a third variation, the suction end 120 comprises a set of suction tubes 124 with a set of openings 125. In other variations, the suction end 120 may have any suitable combination of the above variations, or any suitable configuration to facilitate provision of a negative pressure within the uterus.

The shield 127 functions to provide a barrier, in order to prevent obstruction of the opening(s) of the suction tube 122 or set of suction tubes 124 by uterine tissue or any other substance within the uterus. The shield 127 is preferably coupled to a distal portion of the suction tube 122 or set of suction tubes 124 configured to enter the uterus, but may be coupled to any suitable portion of the suction module 110 or suction tube 122 to prevent obstruction. The shield 127 is preferably composed of a medical-grade material, such as a medical-grade metal or polymer, but may be composed of any suitable material to prevent obstruction of the opening(s). Additionally, the shield 127 may be rigid or flexible.

In a first variation, the shield 127' is configured to couple to a portion of a suction tube 122 and diverge outward from the suction tube 122 at least at a location of an opening 123 to form a perimeter, such that uterine tissue or other tissue is prevented from impinging upon the opening 123. In an example of the first variation, the shield 127' comprises a conical or pyramidal surface 128' that flanks a suction tube 122 and that has an open mouth 129' that extends beyond a distal end of the suction tube 122, as shown in FIG. 2A. In a second variation, the shield 127" may partially encapsulate an opening 123 (e.g., by a cage or a frame) to prevent obstruction of the opening 123. In an example of the second variation, as shown in FIG. 2B, the shield 127" may form a bulbous cage 199" about an opening 123. The dimensions of the bulbous cage are preferably smaller than the atonic uterus, such that sufficient contraction may be enabled, and smaller than the vagina opening, such that correct position may be reached. In another example of the second variation, as shown in FIG. 2C, the shield 127" may form a capsule 198" about an opening, wherein the body of the capsule 198" prevents obstruction of an opening 123 of the suction tube 122, and wherein the capsule has an hole 197" configured to allow the suction tube 122 to facilitate creating of a negative pressure within the uterus. The shield 127 may, however, comprise any suitable geometry and/or configuration to prevent obstruction of the opening(s) of the suction tube 122 or set of suction tubes 124.

In alternative variations, the suction tube 122 or the set of suction tubes 124 may be configured to also function as a shield 127 (or to be physically coextensive with the shield). In these alternative variations, the suction tube 122 or the set of suction tubes 124 thus functions to simultaneously allow a negative pressure to be applied within the uterus, while preventing obstruction of suction tube opening(s). This dual-functionality may be enabled by strategic placement of the opening(s) 123, 125 of the suction tube(s) 122, 124, and/or by geometrically configuring the suction tube(s) to prevent obstruction of an opening or openings.

Figure 3A:
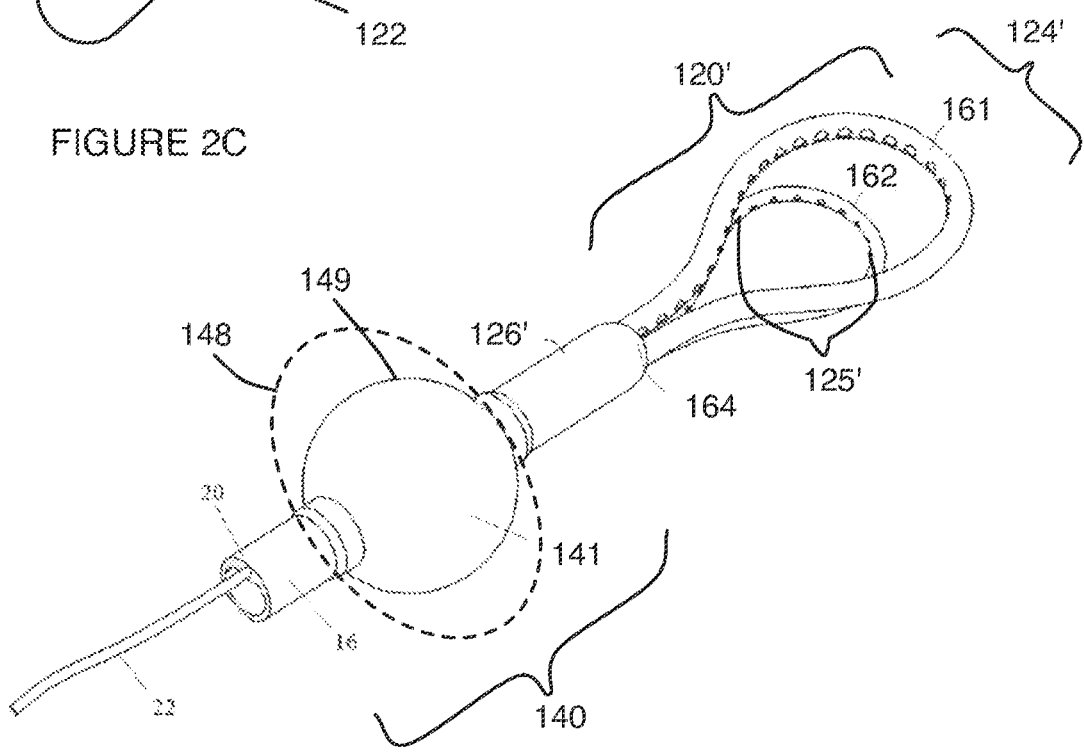
FIG. 3A depicts a specific example of a uterine hemorrhage controlling system.
Figure 3B:
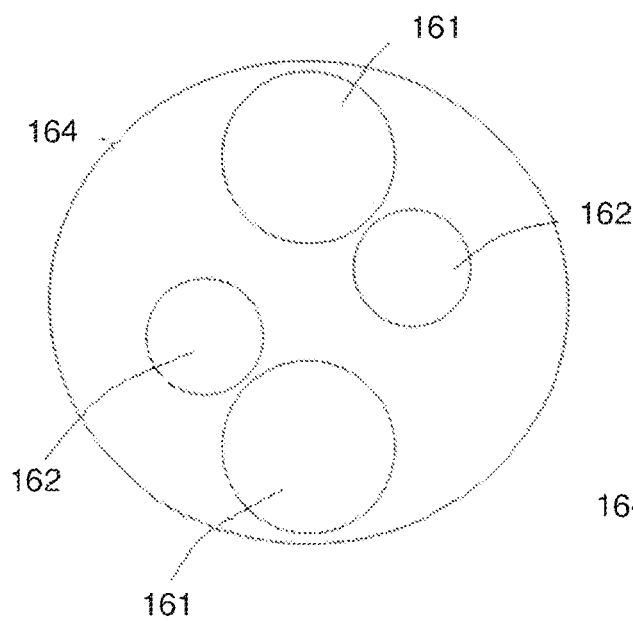
FIGS. 3B and 3C depict cross-sectional views of suction tube connecting joints.
Figure 3C:
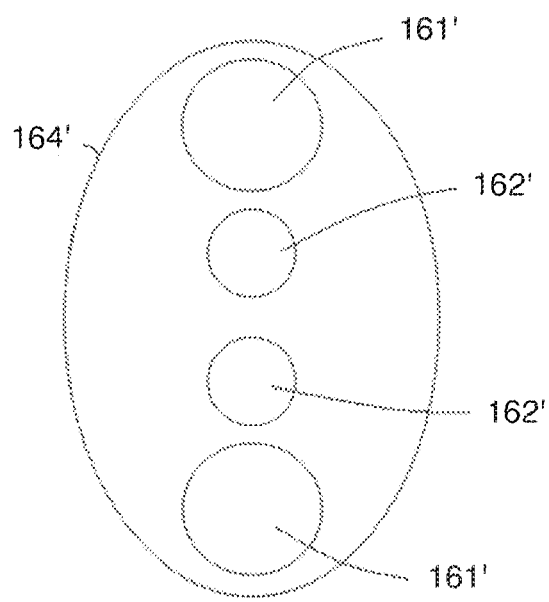

In a first variation of an embodiment wherein the suction tube(s) function as a shield, the suction end 120' may comprise a set of curved suction tubes 124' connected to a connecting tube 126 coupleable to the pump 130, as shown in FIG. 3A. In an example of the first variation, the set of curved suction tubes 124' may comprise a first suction tube 161 and a second suction tube 162 that are arranged in loops that extend different distances. As shown in the cross sections of FIGS. 3B and 3C, the first suction tube 161 and the second suction tube 162 may be coupled to the connecting tube 126 by a joint 164. In the example, the first suction tube 161 may have a longer length and extend in a wider loop from the distal end 112 of the suction module, and the second suction tube 162 may have a shorter length and be configured in a loop that is within the loop created by the first suction tube 161. The first suction tube 161 and the second suction tube 162 in the example may have identical or non-identical cross sections (e.g., dimensions, geometry, lumen configurations), a maximum cross sectional dimension between 25 mm and 125 mm, and substantially smooth surfaces to prevent abrasion within the vagina/uterus. The set of curved suction tubes 124' in the first example is composed of a medical-grade material that is flexible enough to conform to intra-uterine anatomy, but rigid enough to maintain fixed angles at the point of connection between the set of curved suction tubes 124' and the connecting tube 126. The medical-grade material in the example has a Shore A hardness value between 50 and 90. In the example of the first variation, the set of curved suction tubes 124' comprises up to eight suction tubes 122'.

Figure 3D:
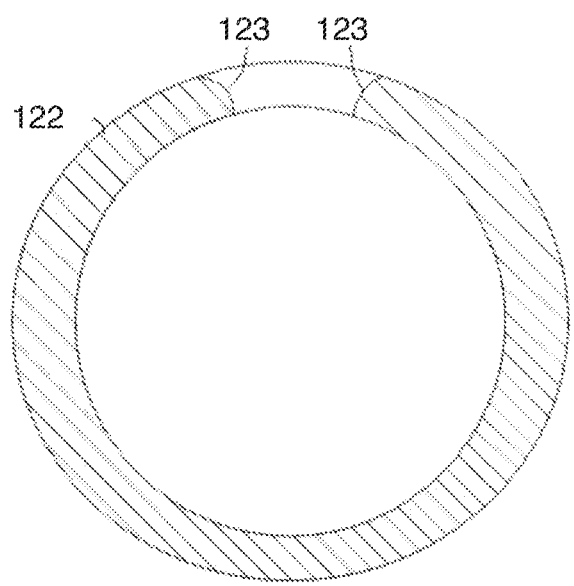
FIG. 3D shows an example of a suction tube cross section and opening.

In the example of the first variation, each suction tube 122' in the set of curved suction tubes 124' comprises a lumen that is coupled, by the connecting tube 126', to the pump 130, and also connected to a set of openings 125'. A negative pressure provided by the pump 130 therefore facilitates uterine contraction and allows intra-uterine fluids to flow through a set of openings 125' into the lumen of a suction tube 122'. The set of openings 125' in the example are oriented to open along a medial surface of a suction tube 161,162 to prevent uterine tissue or other tissue from obstructing the set of openings 125'. The set of openings 125' in the example comprises openings 123' that are between 1 and 6 mm in diameter, and are also substantially smooth and rounded, as shown in the cross-section of FIG. 3D, to prevent damage to the uterus or other tissues.

Figure 4A:
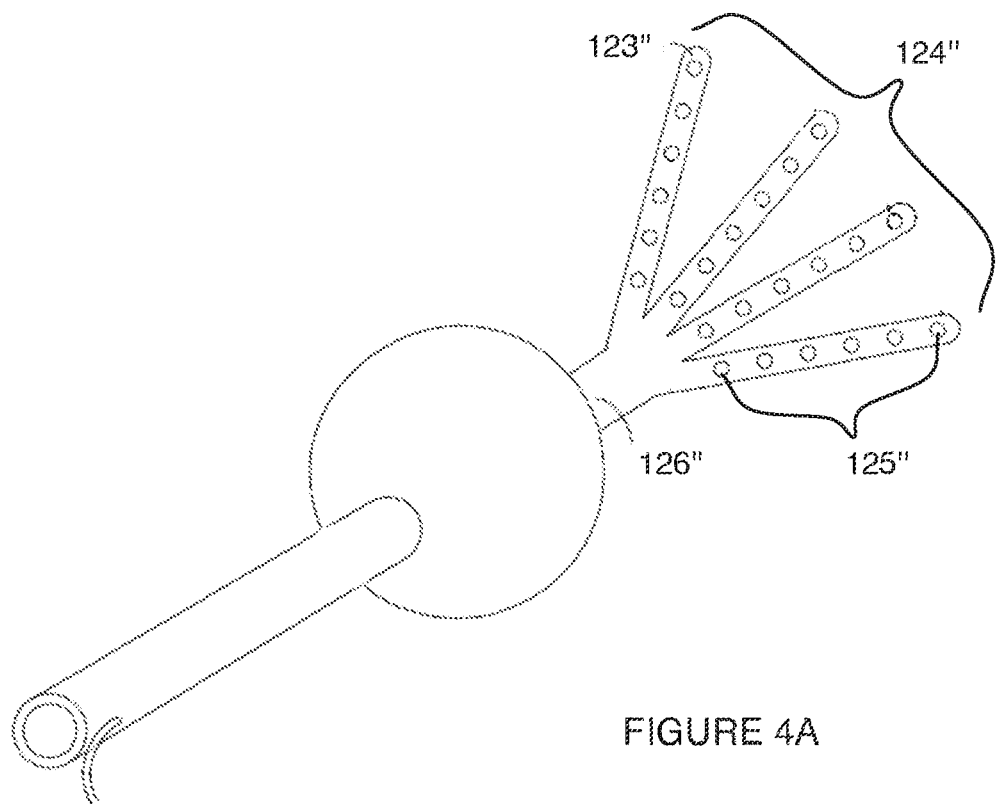
FIGS. 4A and 4B depict examples of suction tubes that also function as shields.

In a second variation of an embodiment wherein the suction tube(s) function as a shield 127, the set of suction tubes 124" branch from the connecting tube 126", and at least one of the set of suction tubes 124" comprises a set of openings 125" along a medial surface of a suction tube of the set of suction tubes 124". The branched configuration functions to prevent tissue from obstructing the medially oriented openings. In an example of the second variation, as shown in FIG. 4A, the set of suction tubes 124" comprises openings 123" that are between 1 and 6 mm in diameter, and up to 16 suction tubes with smooth and/or rounded edges to prevent damage to the uterus or other tissues.

Figure 4B:
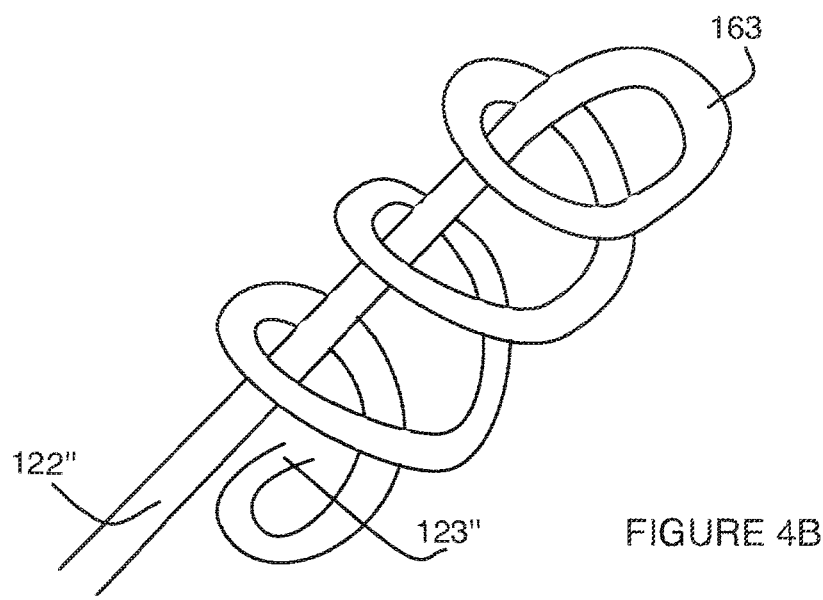

In a third variation of an embodiment wherein the suction tube(s) function as a shield 127, a suction tube 122''' or a set of suction tubes 124''' may comprise a turnabout portion 163 configured to prevent an opening from being obstructed. In an example of the third variation, a turnabout portion 163 of a suction tube 122''' may be configured to wrap around itself along a portion of the length of the suction tube 122''', as shown in FIG. 4B. In another example, a set of suction tubes 124" may comprise a suction tube 122''' with a turnabout portion 163 configured to partially wrap around a length of the set of suction tubes 124'''. Alternatively, the turnabout portion 163 may not be configured to partially wrap about a suction tube 122''', but may still provide a shield 127 by providing a barrier to prevent obstruction of an opening.

Figure 4C:
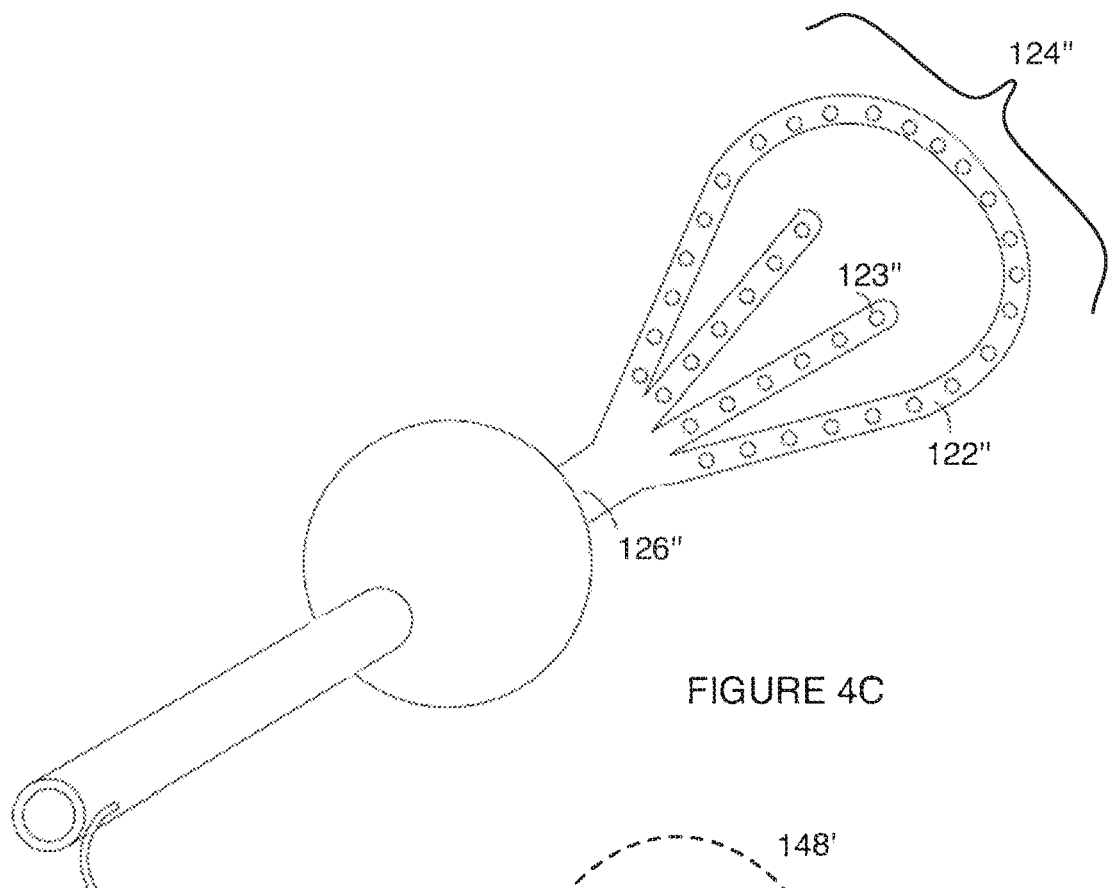
FIG. 4C depicts an example of a system that combines variations of elements.

Other variations of the suction tube(s) 122, 124, shield 127, and/or dual-functioning suction tube(s) may comprise any suitable combination of the above variations, an example of which is shown in FIG. 4C.

1.2 System—Sealing Module

The sealing module 140, which is preferably proximal to the suction end 120 and comprises a deformable seal 142, functions to provide a seal such that negative pressure may be maintained within the uterus to facilitate contraction of the uterus. The sealing module 140 may be configured to provide a seal at any point from the vulva, the cervix, or any point within the uterus, but preferably provides a seal at a point along the vagina distal to the uterus. The sealing module 140 may also be configured to be deformable, such that the sealing module 140 has more than one configuration; however, the sealing module 140 may be configured to be substantially non-deformable, such that the sealing module 140 only has a single configuration.

Preferably, a complete seal (e.g., airtight/hermetic) is provided by the sealing module 140, such that a negative pressure is maintained within the uterus even after the pump 130 is deactivated. In some embodiments, however, a non-complete seal may be provided by the sealing module 140, such that an adequate negative pressure is transmitted to the uterus while the pump 130 is activated, but the negative pressure is not maintained after the pump 130 is deactivated. In some embodiments where a complete seal is not maintained, the system 100 may function to provide adequate vacuum to the uterus provided that the leak rate past the sealing module 140 is less than the pump rate of the pump 130. Thus, for example, in some embodiments, the pump 130 can provide a pump rate that is between 1 L/min-20 L/min, such as between 10-15 L/min. The pump rate can be on the lower end of the range, for example, when the seal is complete and on the higher end of the range, for example, when the seal is not complete.

Figure 16:
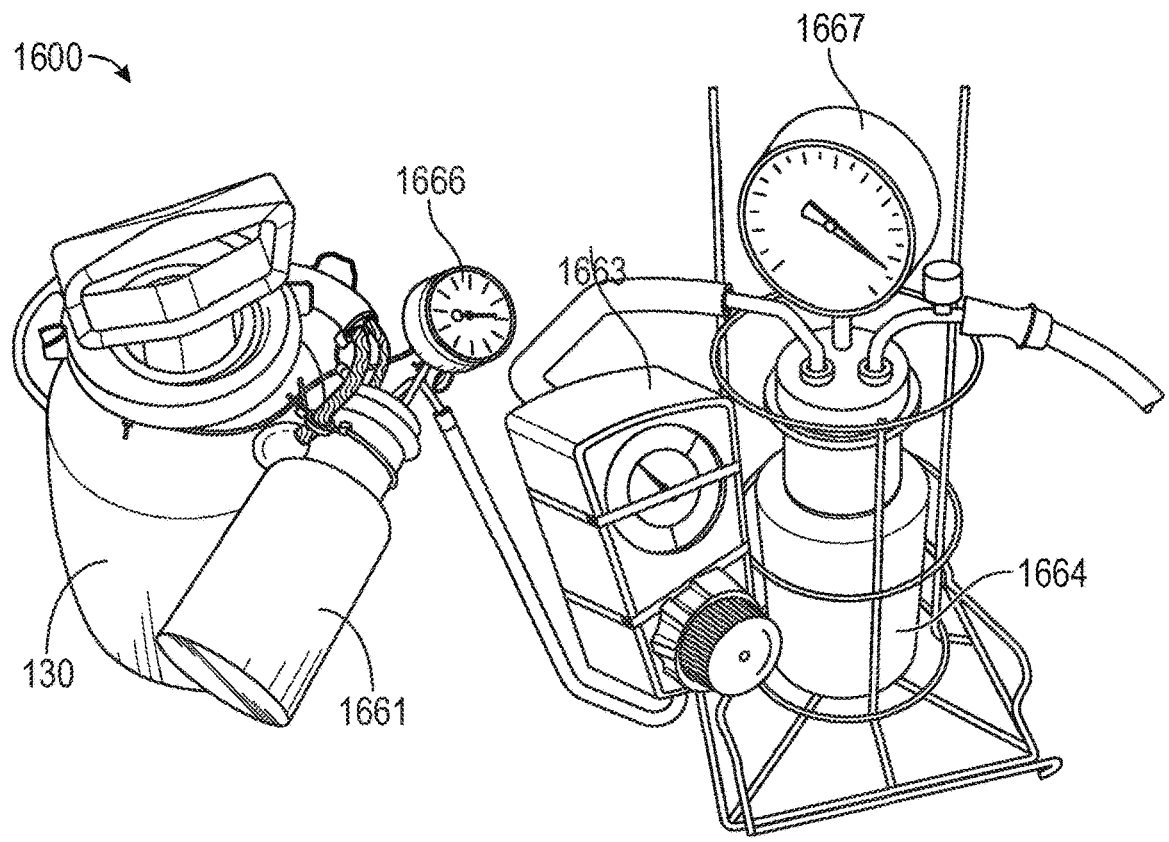
FIG. 16 depicts an exemplary vacuum system with a reservoir.

Alternatively, referring to FIG. 16, in some embodiments, a pump system 1600 can include a manual or intermittent pump 130 with a vacuum reservoir 1661 attached thereto. The vacuum reservoir 1661 can, in turn, be connected to a pressure regulator 1663. A separation canister 1664 can be connected both to the pressure regulator 1663 and to tubing 1665 that leads to the suction module (which can be any suction module described herein). The pump system 1600 in this configuration can be configured to maintain a steady vacuum even if pumping with pump 130 is stopped (e.g., between vacuum pulses). Thus, the pump 130 may be configured to draw a very high vacuum (e.g., substantially higher than the therapeutic 80 mmHg) into the reservoir 1661 while the pressure regulator 1663 can be configured to maintain a relatively constant vacuum (e.g., of 80 mmHg) at the suction module. The gauge 1666 connected to the reservoir 1661 can be configured to indicate when the reservoir 1661 needs to be refilled (i.e., by activation of the pump 130). Further, the separation canister 1664 can be configured to keep blood from reaching the pressure regulator 1663. In some embodiments, the regulator 1663 can include a display configured to indicate the pressure supplied to the suction module. In other embodiments, the canister 1664 can include a gauge 1667 thereon (e.g., if a fixed (non-display) regulator 1663 is used) to indicate the pressure supplied to the suction module. Advantageously, the system 1660 enables the use of intermittent (e.g., manual) pumping, such as in low resource settings without access to electricity or battery power, while still providing a relatively constant vacuum level to the suction module.

At least a portion of the sealing module 140 may be configured to be disposable, and at least a portion of the sealing module 140 may be configured to be reusable.

In a first variation, the sealing module 140 is configured to provide a seal within the vaginal canal and/or at the cervix. In the first variation, the sealing module 140 may comprise a seal 141 that is configured to deform, reversibly or irreversibly, into at least two configurations. A first configuration 148 preferably activates the seal, and a second configuration 149 preferably deactivates the seal. Producing the first configuration may involve an expansion (e.g., radial, axial, uniform, non-uniform, isotropic, non-isotropic) of the seal 141, and producing the second configuration 149 may involve a contraction (e.g., radial, axial, uniform, non-uniform, isotropic, non-isotropic) of the seal 141. Producing the first configuration 148 may alternatively involve releasing a constrained seal 141, and producing the second configuration may involve constraining a released seal 141. However, the seal 141 in the first variation may be a non-deformable seal that has a single configuration.

Figure 5A:
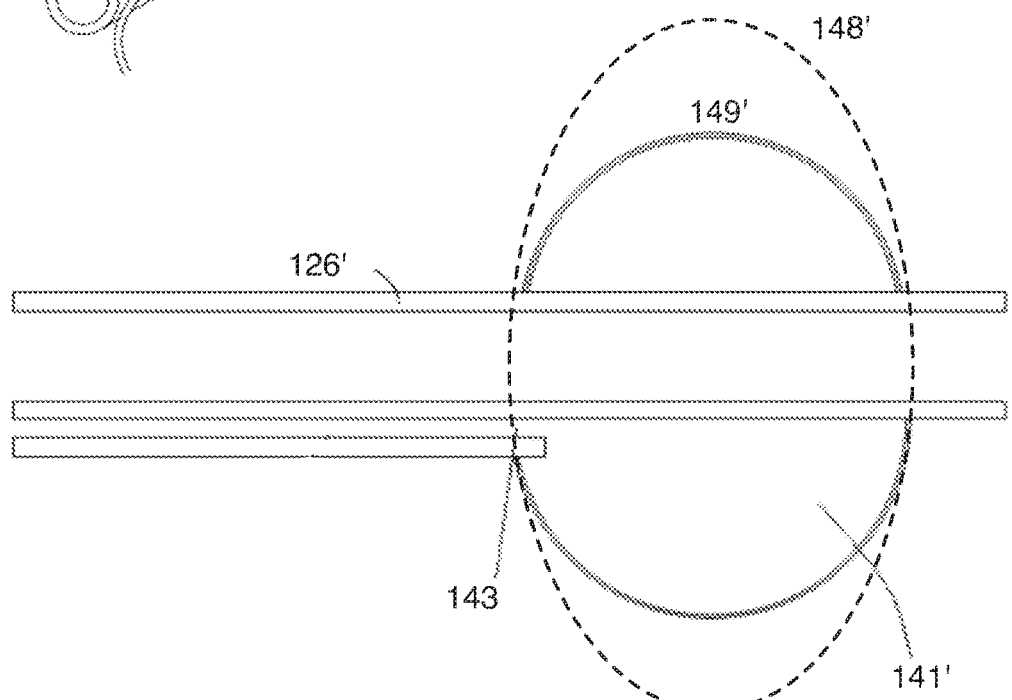
FIGS. 5A-5B depict examples of an inflatable sealing module element.
Figure 7:
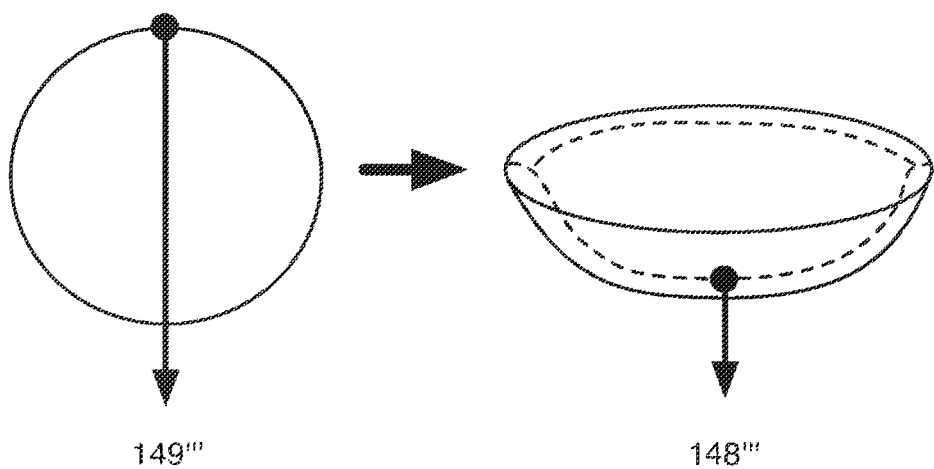
Figure 8A:
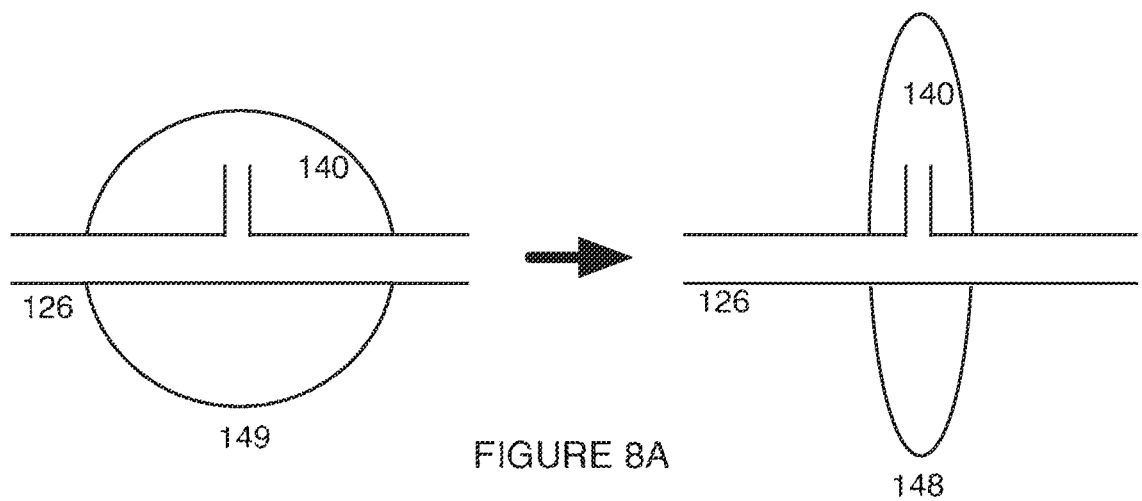
FIGS. 8A and 8B depict examples of system elements with dual functionality.

In a first specific example of the first variation, as shown in FIGS. 3A and 5A, the seal 141' is an inflatable balloon configured to deform into an expanded configuration 148' and a contracted configuration 149'. Upon delivering the suction end 120 transvaginally, the seal 141' in the first specific example is configured to be situated, in the contracted configuration 149', within the vaginal canal. The seal 141' may then be expanded to produce an expanded configuration 148' that seals the vagina in order to facilitate maintenance of a negative pressure within the uterus. In the first specific example, the seal may be expanded isotropically by delivering a fluid (e.g., saline or water) or a gas (e.g., air, nitrogen) to the interior of the inflatable balloon from a source external to the seal through an opening into the inflatable balloon. As shown, the balloon seal 141' in the expanded configuration 148' can have an elongated shape, such as an elongated sphere or spheroid. Alternatively or additionally, the balloon seal 141' may have a disk or semi-spherical shape (as shown in FIGS. 7 and 8A). The expanded configuration 148' of the seal in the first specific example substantially fills the entire cross section of the entrance of a woman's postpartum uterus (e.g., the balloon inflates to have a volumetric capacity up to 300 milliliters, the balloon inflates to have a volumetric capacity greater than 300 milliliters), and has a diameter between 5 and 14 cm (with a mean diameter of approximately 10 cm). The inflatable balloon in the first specific example can also withstand an internal pressure of at least 5 psi, and can be reversed to a contracted configuration 148' upon delivery of the fluid or gas from the interior of the inflatable balloon.

In the first specific example, the inflatable balloon can be compliant or non-compliant. When compliant, the balloon may conform to the anatomy and provide enhanced comfort for the patient. When noncompliant, the balloon may impose on surrounding anatomy to create a stronger seal and/or to help the device stay in place.

Figure 5B:
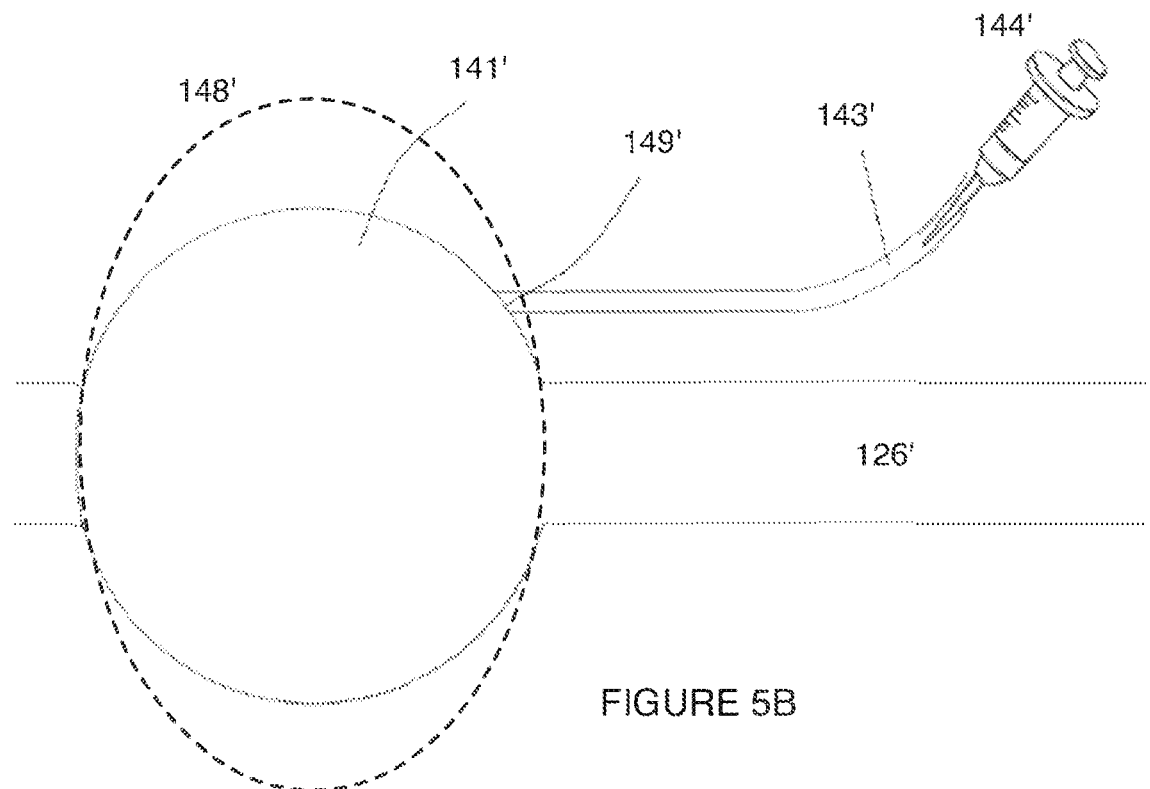

In the first specific example, as shown in FIGS. 5A and 5B, the inflatable balloon surrounds the connecting tube 126 coupled to the suction end 120, such that the connecting tube 126 is isolated from and passes entirely through the inflatable balloon. A separate delivery conduit 143, coupleable to a fluid or gas source 144, then transfers a gas or fluid through an opening into the inflatable balloon. The delivery conduit in the first specific example is composed of silicon, but may alternatively be composed of any other suitable material (e.g., rubber, plastic, silicone, silastic, plastic, polyethylene, polyurethane).

In the first specific example, the seal 141 may alternatively be expanded by producing a chemical reaction (e.g., mixture of an acid with a base, or any reaction that produces a volumetric expansion) within the interior of the sealing balloon. For instance, an acidic solution may be isolated from a chemical base within the sealing balloon, and upon mixture of the acidic solution with the chemical base, a resulting chemical reaction may produce a controlled, volumetric expansion of the sealing balloon by the production of a gas within the sealing balloon.

Figure 6:
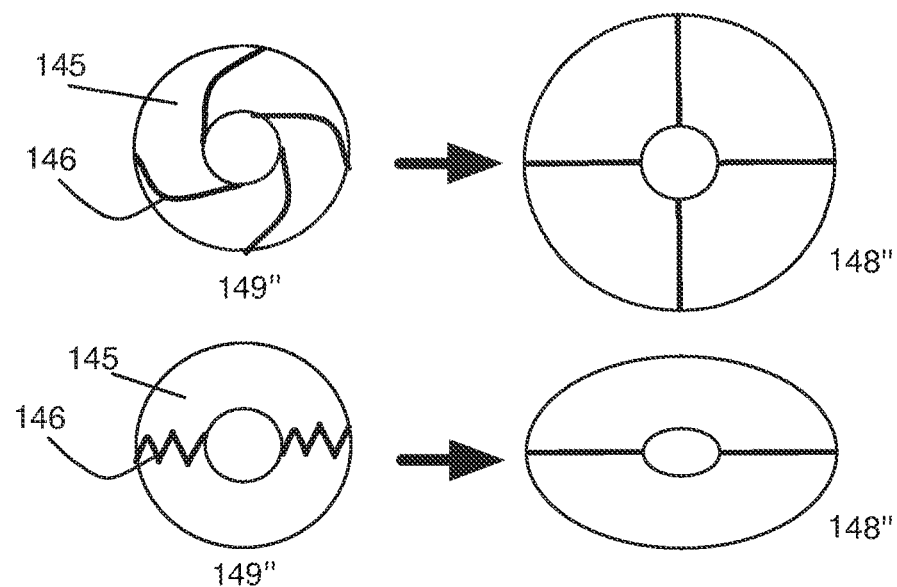
FIGS. 6 and 7 depict examples of sealing module variations.

In a second specific example of the first variation, the seal 141" comprises a membrane 145 and at least one deformable member 146, and is configured to expand radially outward into a first configuration 148" and to contract radially inward into a second configuration 149" upon manipulation of the deformable member 146. Upon delivering the suction end 120 transvaginally, the seal 141" in the second specific example is configured to be situated in the second configuration 149", within the vaginal canal. As shown in FIG. 6, the deformable member 146 may be configured to produce an expansion in one, two, or three dimensions (e.g., upon release of a compressed elastically deformable member), and to produce a contraction in one, two, or three dimensions (e.g., upon compression of an elastically deformable member). Alternatively, the deformable member 146 may be a brace attached to the membrane 145 that can outwardly push the membrane 145 into the first configuration 148" and can inwardly pull the membrane 145 into the second configuration 148". In another alternative version of the second example, the deformable member 146 may be a shape-memory material, such as nitinol, that outwardly pushes the membrane 145 into a first configuration 148" in one environment (e.g., within the body), and inwardly pulls the membrane 145 into a second configuration 148" in another environment (e.g., outside of the body).

In a third specific example of the first variation, the seal 141'" is configured to take on a first geometric configuration 148'" upon an axial deformation of the seal 141' and to take on a second geometric configuration 149'" in response to a reverse deformation of the seal 141". Upon delivering the suction end 120 transvaginally, the seal 141'" in the third specific example is configured to be situated, in the first geometric configuration 149', within the vaginal canal. In the third specific example, the seal 141'" may be structurally configured with a wall that produces a sealing configuration 148'" upon axial deformation and to produce a non-sealing configuration 149'" upon removal of the axial deformation, as shown in FIG. 7. The wall may further comprise ridges or other structures that control deformation into the sealing configuration 148". Alternatively, the seal 141' may be composed of an incompressible, deformable material, such that axial deformation produces an outward expansion to form the seal, and removal of the axial deformation results in an inward contraction that reverses the seal. In another alternative version of the third example, the seal 141'" may comprise a shape-memory material, such as nitinol, that forms a sealing configuration 148'" in one environment (e.g., within the body), and forms a non-sealing configuration 149'" in another environment (e.g., outside of the body).

In a fourth specific example of the first variation, the seal 141"" comprises a porous material (e.g., sponge, polymer hydrogel) that is configured to deform into an expanded configuration 148"" upon absorption of a fluid, and to be in a non-expanded configuration 149"" in the absence of a fluid. The porous material may be inserted into the body in a non-expanded configuration 149"" and may form the expanded configuration 148"" of the seal upon absorption of blood, uterine fluids, or any other fluids. The seal 141"" of the fourth example may thus further function to control blood loss/hemorrhaging by absorbing blood.

In a second variation, the sealing module 140 is configured to provide a seal at the vulva in an extracorporeal manner. In an example of the second variation, the sealing module 140 comprises a membrane 145 configured to seal the entrance to the vagina external to the body. The membrane 145 has an area larger than the entrance to the vagina, such that an adequate seal may be formed. The sealing module 140 may further comprise a sealant (e.g., gel or lubricant) placed between the membrane 145 and the body, such that a hermetic and airtight seal is formed at the vulva. In this manner, the entrance to the vagina is substantially sealed to allow a negative pressure to be provided within the uterus.

In other variations, the sealing module 140 may only have a single configuration 148 configured to produce a seal upon insertion into the body. Prior to insertion, the vagina or vaginal canal may be manually expanded (e.g., with a speculum operated by a health care provider), the sealing module 140 may be inserted (with the suction end 120 already inserted), and the vagina or vaginal canal may then be released to form a seal about the sealing module 140. In an example, the sealing module 140 is a substantially rigid structure that has a cross section larger than the cross section of the vaginal canal, such that the vaginal canal seals around the rigid structure.

Figure 8B:
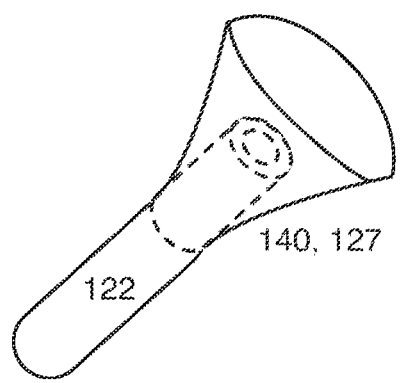

Additional variations of the sealing module 140 may comprise any suitable combination of the above variations, or combination of any of the above variations with any other suitable sealing element. Furthermore, in other variations, as shown in FIG. 8A, the connecting tube 126 of the suction module 110 may be coupled to the sealing module 140, such that a negative pressure provided by the suction module 110 contracts the uterus and produces a sealing configuration by the sealing module 140. Additionally, other variations may comprise a sealing module 140 that functions as a shield 127 (or is physically coextensive with a shield), an example of which is shown in FIG. 8B. Again, the sealing module may comprise any suitable combination or configuration of elements as described.

The sealing modules described herein can be placed in the lower uterus, cervix, vaginal canal or at the outer surface of the body at the vulva to maintain vacuum within the uterus. In some embodiments, the device can be configured such that the natural collapse of the postpartum tissue in the cervix and vagina creates an adequate seal (i.e., without the sealing module). Sealing the lower uterus, cervix, vaginal canal, or outer surface of the body can hinder the flow of air into the uterus while vacuum is being applied in order to achieve a therapeutic isobaric level of vacuum throughout most if not all of the uterus.

1.3 System—Other Elements

As shown in FIG. 1, the system 100 may further comprise a pump 130, which functions to generate the negative pressure in order to contract the uterus. The pump may comprise a clinical (e.g., hospital) suction line, vacuum device, or any appropriate pump (e.g., syringe pump, peristaltic pump) that can produce an adequate negative pressure to contract the uterus. In a specific example, the pump generates a negative pressure within the uterus of up to 3 psi. In one variation, the connecting tube 126 of the suction module 110 is configured to couple to the pump 130 in a reversible manner. However, the connecting tube 126 may also terminate in a pump element in a non-reversible manner, such that the pump 130 is integrated with the system 100. In an example, the pump element is a hollow chamber with a naturally expanded configuration. The pump element in the example may be constrained in a depressed state prior to delivering the suction end 120 into the uterus, after which the pump element is released to expand freely. Expansion of the pump element thus generates the negative pressure required to facilitate contraction of the atonic uterus.

Also shown in FIG. 1, the system 100 may further comprise a filter 150, which functions to filter fluids and other substances that have entered the connecting tube 126. The filter is preferably distal to the pump 130 and proximal to the suction end 120, such that any substance that enters the suction end 120 is filtered prior to reaching the pump 130. Alternatively or additionally, the opening(s) of the suction end 120 may comprise filters that function to pre-filter substances that enter the suction end 120. The filter 150 preferably comprises a membrane with pores that prevent passage of unwanted substances into the pump.

As a person skilled in the art will recognize from the previous detailed description and from the figures and claims, modifications and changes can be made to the preferred embodiments of the system without departing from the scope of this invention.

2. Method

Figure 9:
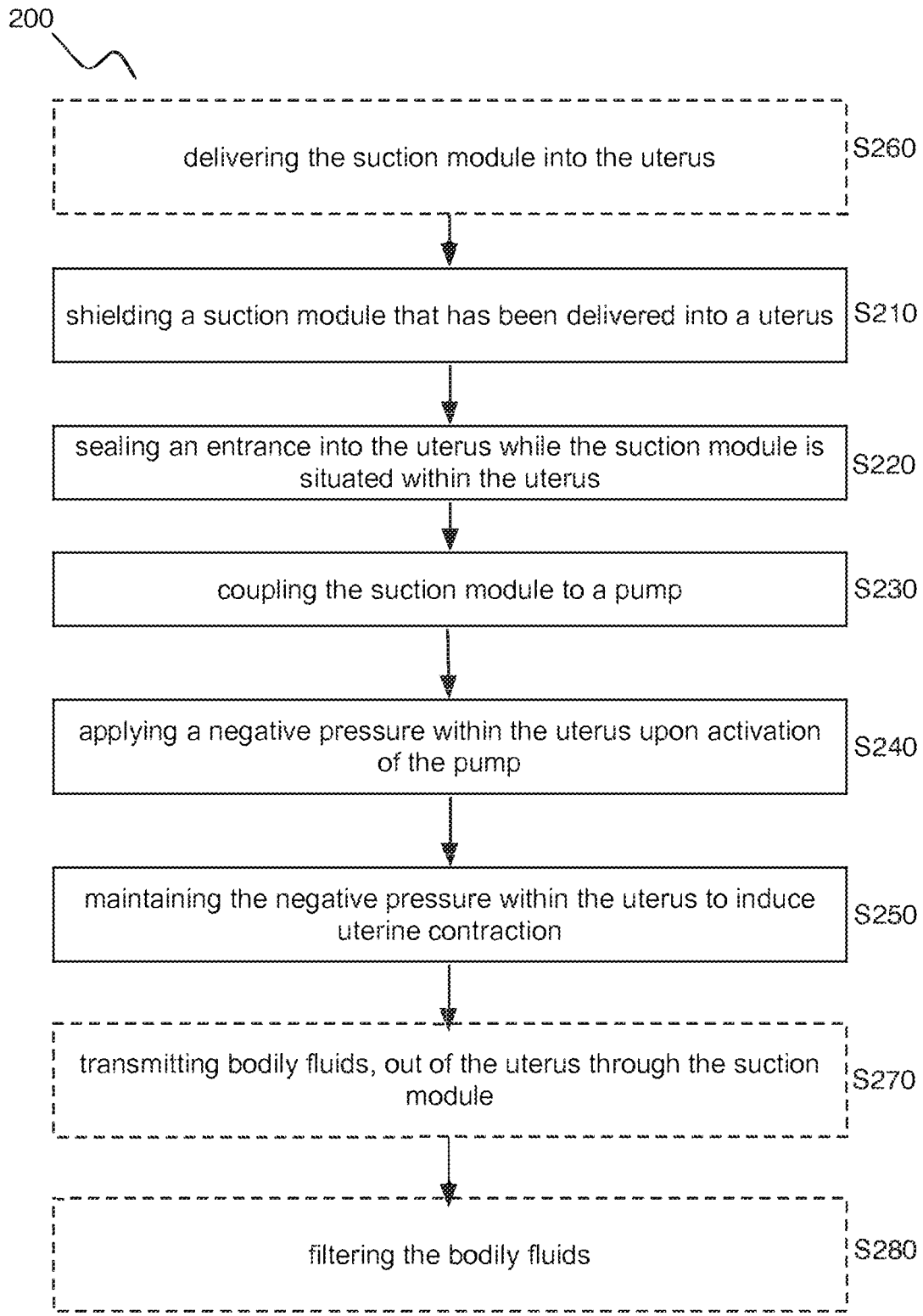
FIG. 9 depicts an embodiment of steps of a uterine hemorrhage controlling method.

As shown in FIG. 9, a uterine hemorrhage controlling method 200 comprises: shielding a suction module that has been delivered into a uterus S210, sealing an entrance into the uterus while the suction module is situated within the uterus S220; coupling the suction module to a pump S230; applying a negative pressure within the uterus upon activation of the pump S240; and maintaining the negative pressure within the uterus to induce uterine contraction S250. The method 200 may further comprise delivering the suction module into the uterus S260; transmitting bodily fluids out of the uterus through the suction module S270, and/or filtering the bodily fluids S280.

Applying vacuum (e.g., a pressure of 40-160 mmHg, such as 50-100 mmHg, such as 70-90 mmHg, such as approximately 80 mmHg) to a postpartum uterus as described herein can have the initial effect of removing liquid blood and other fluids, as well as potentially removing clotted blood, from the uterus while collapsing the uterine walls onto themselves. The stimulation of the uterine walls with the vacuum and the tissue contraction that comes from collapsing the uterine walls may facilitate the eventual return of tone and full contraction of the myometrium, enabling the natural mechanism of pinching the arterial vessels to physiologically stop bleeding. The method 200 can thus function to reduce or entirely stop uterine hemorrhaging, in order to substantially reduce total blood lost from the uterus after childbirth. The method 200 may further function to reduce other issues associated with childbirth, including a need for a blood transfusion or a hysterectomy. Furthermore, because the method 200 is performed transvaginally, a patient may remain conscious while the method 200 is performed. The method 200 is preferably performed by the system 100 described above or using the system 100 described above; however, the method 200 may be performed by or using any other suitable system.

Step S210 recites shielding a suction module that has been delivered into a uterus, and functions to prevent obstruction of a suction module opening, such that a negative pressure may be applied to the interior of the uterus. Preferably, Step S210 is performed using any suitable variation of the shield and/or dual-functioning suction end described above. For example, Step S210 may be implemented using a shield to shield the suction tube, or may be implemented using a suction tube with medially oriented openings, such that the suction tube dually functions as a shield. However, Step S210 may be formed using any suitable element or method to prevent uterine tissue or any other tissue from blocking an opening of the suction module.

Step S220 recites sealing an entrance into the uterus while the suction module is situated within the uterus, and functions to enable maintenance of a negative pressure within the uterus. Preferably, Step S220 is performed using any suitable variation of the sealing module described above, an example of which is shown in FIG. 10; however, Step S220 may be formed using any suitable element or method configured to seal an entrance into the uterus. In a first example, Step S220 comprises expanding an inflatable balloon seal (e.g., by delivering fluid or gas into the balloon) at the entrance to the uterus. In the first example, the inflatable balloon may be inflated near the distal end of the vagina to a pressure of up to 5 psi. In a second example, S220 comprises producing a radial expansion of a membrane seal. In a third example, S220 comprises axially deforming a seal to transform the seal into a sealing configuration. In a fourth example, S220 comprises applying a sealant external to the vaginal canal and placing a sealing membrane at the entrance to the vaginal canal to create a seal. In a fifth example, S220 comprises manually expanding the vaginal canal, placing a sealing element into the vaginal canal, and then allowing the vaginal canal to contract about the sealing element to create the seal. Other variations of S220 may comprise other manipulations of system variations described above, or any other suitable method of sealing an entrance to the uterus.

Figure 12:
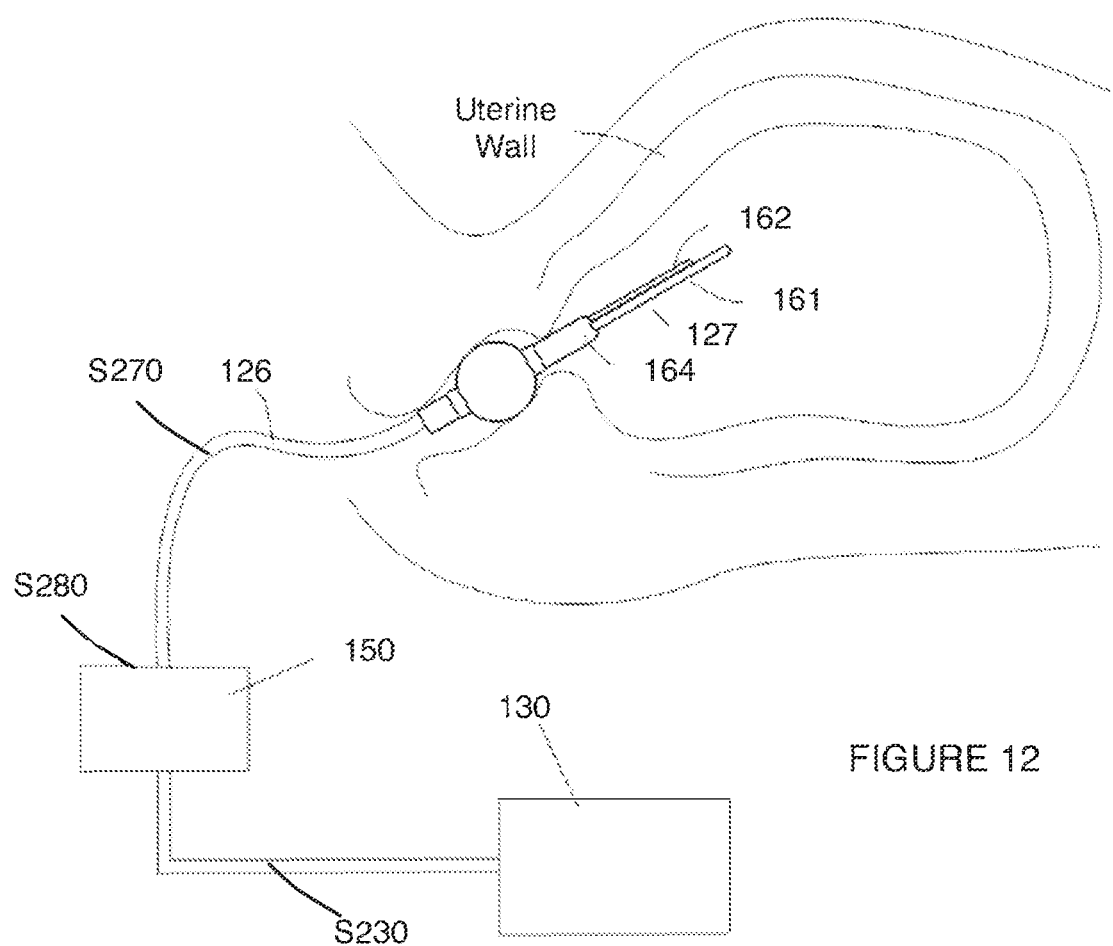
FIG. 12 is a schematic showing an implementation of an embodiment of a uterine hemorrhage controlling method.

Step S230 recites coupling the suction module to a pump, and functions to prepare the suction module to transmit a negative pressure to the interior of the uterus. Step S230 may be performed before or after the suction module has been delivered to the interior of the uterus. In one variation, Step S230 may comprise coupling a connecting tube of the suction module to a clinical suction line, as shown in FIG. 12, but in other variations, Step S230 may alternatively comprise coupling any suitable portion of a suction module to any suitable pump element. In some embodiments, for example, the suction model can be connected directly to the pump without connecting to an intermediate connecting tube or suction line.

Step S240 recites applying a negative pressure within the uterus upon activation of the pump, and functions to generate a stimulus that enables an atonic uterus to contract, thus counteracting uterine atony. The negative pressure may result in a uniform mechanical stimulus or a non-uniform mechanical stimulus that results in contraction of the uterus to control hemorrhaging. For instance, the negative pressure may be a hydrostatic pressure. In an example, the pump is activated to produce a flow rate of less than 30 liters per minute (e.g., between 1 L/min-20 L/min, such as between 10-15 L/min), and a negative pressure of up to 3 psi within the uterus, while monitoring pressure levels using a pressure sensor.

Step S250 recites maintaining the negative pressure within the uterus to induce uterine contraction, and functions to facilitate closing of exposed uterine arterioles in the uterine wall. That is, applying vacuum to the atonic uterus can achieve initial cessation of bleeding by cutting off the blood flow from arteries normally feeding the utero-placental interface. Application of such vacuum to the uterine cavity by use of a seal in the canal leading to the uterus or by relying on the tissues of the canal to effectively seal around the device can create an essentially isobaric condition within the uterus, affecting all bleeding arteries on the surface of the uterus. Maintenance of this essentially isobaric condition can help control bleeding until full contraction of the uterine wall occurs naturally. In some embodiments, the vacuum level can be 40-160 mmHg. Application of too high of a vacuum level (e.g., above 160 mmHg) can interfere with achieving isobaric conditions due to the propensity for tissue to stick to the vacuum ports in an occlusive manner thus preventing further distribution of vacuum in the uterus. In some embodiments, a vacuum level within 40-160 mmHg can be preset in the system. Step S250 may further function to decrease the possibility of the uterus returning to an atonic state.

Figure 15A:
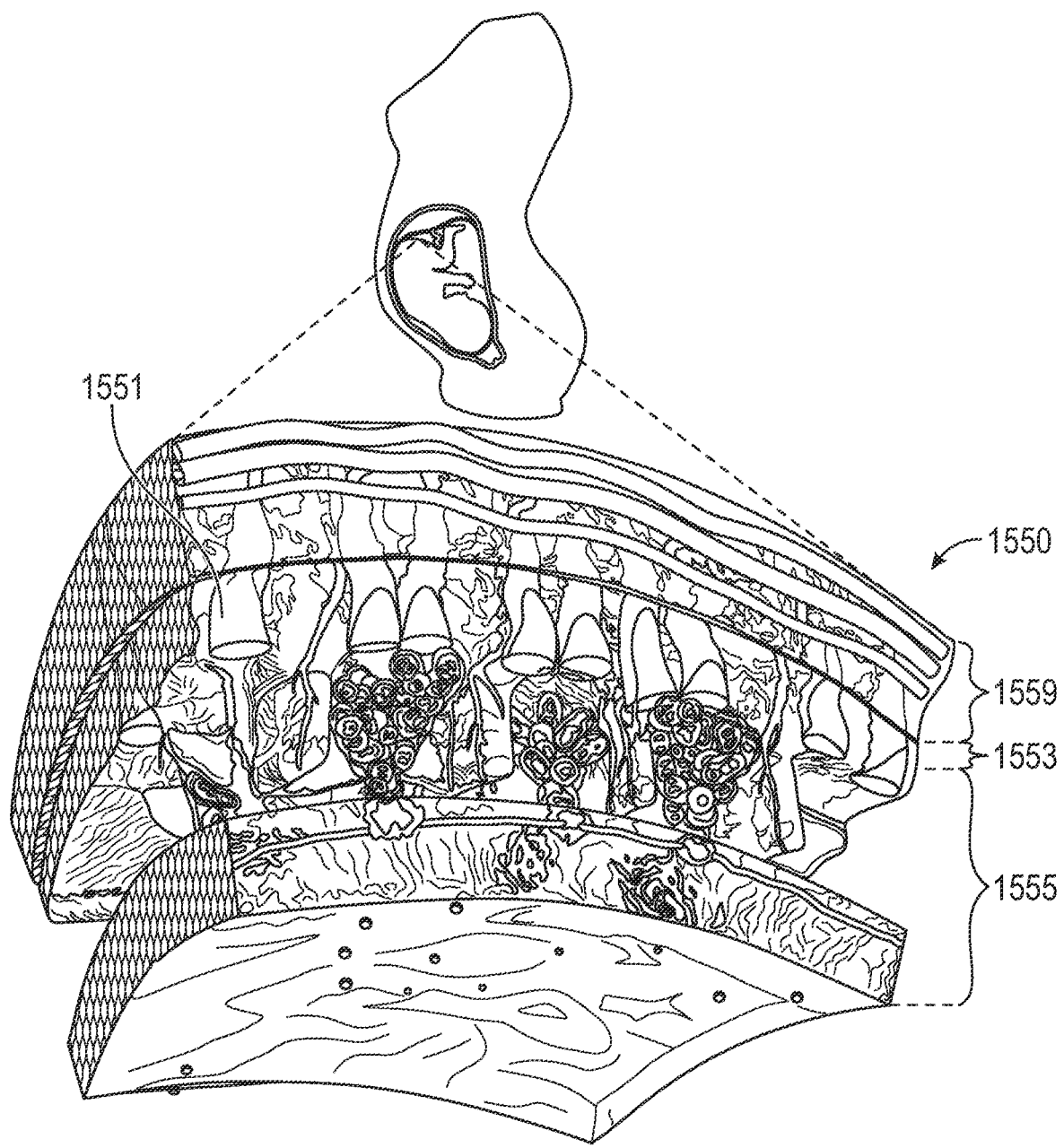
FIG. 15A is a diagram of the uterine wall during pregnancy.
Figure 15B:
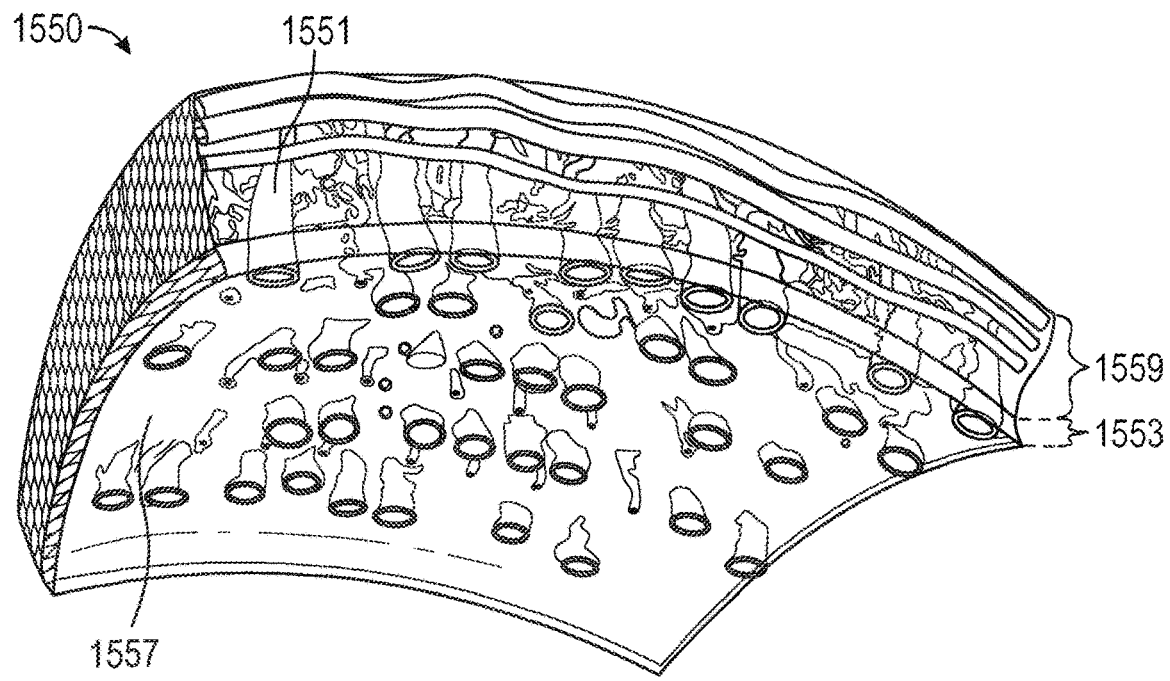
FIG. 15B is a diagram of the uterine wall post-partum.

Referring to FIGS. 15A-15B, advantageously, the systems and methods described herein can control and stop the flow of blood from the utero-placental arteries by applying vacuum to uniquely remodeled spiral arteries 1551 in the endometrium 1553 of the uterine wall 1550, causing them to collapse and thus occlude blood flow by pinching off the arteries 1551. This collapse and occlusion can occur as a result of the vacuum penetrating superficially into the walls of the endometrium 1553, such as by way of the multitude of arteries 1551 that are causing the bleeding condition. As the conduits through which the vacuum is applied become unable to supply blood and fluids to the surface 1557 of the uterus, the natural reaction of the superficial tissue and/or uterine muscle 1559 is to collapse or contract, leading to compression of the walls of the arteries 1551 and hence cessation of bleeding. An additional facilitator for creating this compressive superficial layer may be the actual apposition of the uterine walls 1550 that have come together due to the vacuum.

Macroscopically, the unique remodeling through gestation that enables this mechanism may be the normally spiral arteries 1551 in the endometrium 1553 elongate and remodel to a trumpet shape as the pregnancy progresses. The trumpet shape is unique in that the diameter of the artery 1551 increases in the direction of flow toward the placenta 1555, whereas normally, arterial vessels get smaller in diameter in the direction of flow. The trumpet shape of the arteries 1551 has the effect of slowing the blood velocity while also dramatically decreasing the pressure relative to the flow upstream of the trumpet structure consistent with conventional fluid dynamics. The trumpet shape of the arteries 1551 has the key characteristic of providing an increased surface area on the inside of the arteries 1551 in a low flow condition. The vacuum applied to this increased surface area at the utero-placental interface 1557 can create a collapsing force on the arteries 1551 due to the induced low pressure applied to the inside of the arteries 1551. Furthermore, the relatively slower blood velocity can make it less likely that blood flowing from the feeding arteries is able to replenish the blood that is flowing toward the vacuum in the arteries 1551 before collapse of the arteries 1551 causes a circuitous path through which the blood can no longer flow leading to occlusion. Maintaining the application of isobaric vacuum in the uterus can thus create an omnidirectional cessation of blood flow at every utero-placental interface 1557 until the uterus can eventually attain enough tone to pinch the arteries 1551 as is supposed to naturally occur. This cessation of blood flow can advantageously be used in patients suffering atony and, in some embodiments, in patients suffering disseminated intravascular coagulation (DIC) because the control of bleeding at the collapsed trumpet arteries 1551 is not dependent on coagulation to stop the bleeding.

The application of vacuum described herein can be slow and intermittent (e.g., via hand pump), fast intermittent (e.g., via diaphragm, piston, peristaltic), or steady-state (e.g., via impeller, multiple pistons). The vacuum acting on the tissue can be such that: (1) the period of any cyclic pulses are faster than the time required for the collapsed vessel to recover to patency (e.g., less than 250 mSec); and/or (2) the vacuum within the uterus is maintained at a level that is within 10%, such as within 5%, of a preset vacuum level. Maintaining the vacuum in such a way can advantageously prevent oozing or pulsatile release of blood from the arteries and/or uterus.

Preferably, the negative pressure is maintained until hemorrhaging has been reduced to safe levels or has substantially stopped. The negative pressure may also be maintained as long as deemed necessary to maintain the uterine contraction, and in a specific example, is maintained for between 1 and 24 hours. In an example, maintenance of a negative pressure of 3 psi within the uterus causes the uterus to fully contract within 15 seconds. Additionally, Step S250 may comprise monitoring a patient's blood pressure and heart rate while the negative pressure is maintained, and eliminating the negative pressure after levels have returned to a normal level. In an example, the negative pressure may be eliminated once the patient's systolic blood pressure is between 90 and 140 mm Hg, and the patient's heart rate is between 40 and 100 beats per minute. The negative pressure is preferably eliminated once hemorrhaging has been reduced to safe levels or has substantially stopped. For example, the negative pressure can be removed after the postpartum hemorrhaging and/or abnormal postpartum uterine bleeding is controlled for at least 1 hour, until the uterus is firm, and/or until the patient is stable. The negative pressure may be eliminated by removal of a seal to the entrance to the uterus, which may be performed in any suitable manner (e.g., deflation of an inflatable balloon seal, radial contraction of a membrane, etc.). In some embodiments, the device can be left in place even after hemorrhaging has been reduced (e.g., for up to 24 hours) so as to enable use of the device again should atony return. Advantageously, because the suction module has a low profile (e.g., is relatively flat), the suction module can be both less prone to being ejected from the patient with contraction and more comfortable, thereby enabling prolonged residence within the body.

Figure 11:
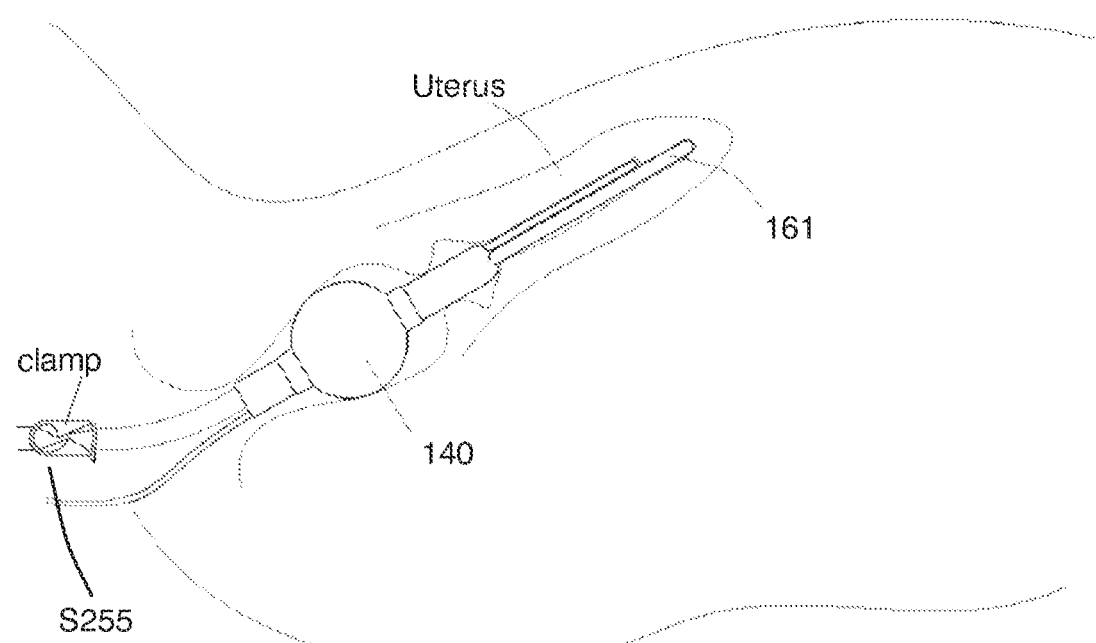

As shown in FIG. 11, Step S250 may further comprise Step S255, which recites obstructing a connection between the suction module and the pump. Step S255 functions to maintain a negative pressure within the uterus, even upon deactivation of the pump. Step S255 also functions to prevent premature elimination of a negative pressure within the uterus (e.g., upon deactivation of the pump). Step S255 may further function to allow intrauterine tissue to re-energize, and may further function to facilitate removal of the suction module from the uterus. In one variation, Step S255 may comprise clamping a connecting tube between the suction module and the pump, as shown in FIG. 11. In another variation, the connection may be a valved connection, such that Step S255 comprises shutting a valve to obstruct a connection between the suction module and the pump. Step S255 may, however, comprise any suitable variation of obstructing a connection between the suction module and the pump.

Figure 10:
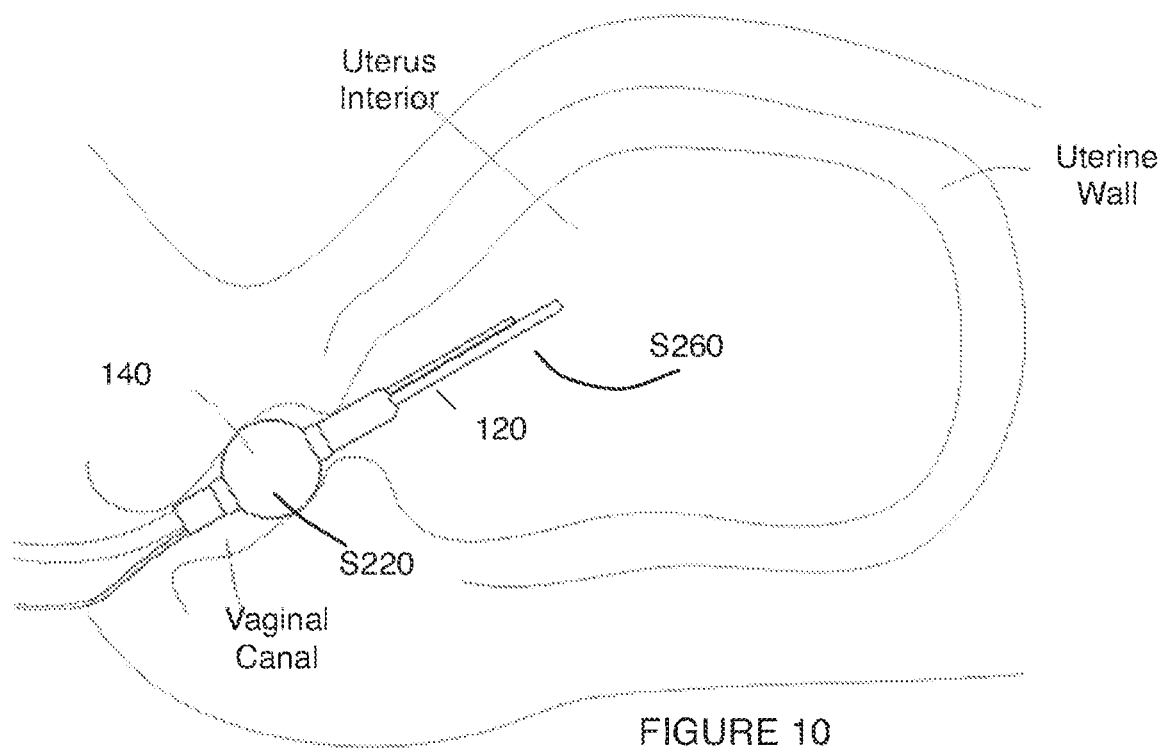
FIGS. 10-11 depict embodiments of steps of a uterine hemorrhage controlling method.

As shown in FIGS. 9 and 10, the method 200 may further comprise Step S260, which recites delivering the suction module into the uterus. Step S260 functions to initiate treatment of an atonic uterus. Preferably, Step S260 comprises delivering the suction end of the suction module described above into the uterus; however, Step S260 may comprise delivering any suitable suction module into the uterus. The reverse of Step S260, as shown in FIG. 11, may comprise removing the suction module from the uterus, and in an example, may comprise clamping a connecting tube to the suction module, deactivating the pump, and then withdrawing the suction module from the uterus. Other variations of Step S260 and the reverse of Step S260 may comprise any other suitable methods of delivering the suction module into the uterus and removing the suction module from the uterus.

As shown in FIGS. 9 and 12, the method 200 may further comprise Step S270, which recites transmitting bodily fluids out of the uterus through the suction module. Step S270 functions to remove fluids from within the uterus in the process of inducing contraction of an atonic uterus. The bodily fluids preferably pass into at least one opening of the suction module and into the connecting tube of the suction module; however, Step S270 may alternatively comprise any other means for transmitting bodily fluids out of the uterus. In some embodiments, the connecting tube and/or portions of the suction module can be translucent or transparent. Having a translucent or transparent portion can advantageously help visualize the flow as the bodily fluids are removed from the uterus. The visualization can enable detection, for example, of fluid flow (e.g., to determine when hemorrhaging has stopped) and/or of air in the tube (which can indicate a leak of the sealing module). In some embodiments, the visualization of blood flow can be used in conjunction with other physical indicators that bleeding is being controlled (such as hardening of the uterus due to contraction or palpating the drop of the fundus below the umbilicus) to determine the efficacy of the treatment and/or to determine when treatment is complete.

Also shown in FIGS. 9 and 12, the method 200 may further comprise Step S270, which recites filtering the bodily fluids. In some embodiments, Step S280 can function to remove particles of a particular size and/or to separate liquids and solids from gas so as to prevent unwanted substances from entering the pump, which allows the pump to maintain proper function and to continually apply a negative pressure. Step S280 may further function to enable monitoring of blood loss. For example, filtering the bodily fluids S280 into a transparent container may include collecting the fluid so as to allow a caretaker to monitor a quantity of blood lost during implementation of the method 100. As another example, collecting or filtering the bodily fluids S280 can enable monitoring of blood flow out of the body (e.g., to determine when hemorrhaging has ceased). As another example, collecting or filtering the bodily fluids S280 into a container may enable further use of the bodily fluids (e.g., for reintroduction into the patient's bloodstream).

Step S280 may occur at any point along the suction module, distal to the pump; however, Step S280 preferably occurs along a connecting tube coupled to the pump.

The FIGURES illustrate the architecture, functionality and operation of possible implementations of systems and methods according to preferred embodiments, example configurations, and variations thereof. In this regard, each block in the flowchart or block diagrams may represent a module, segment, or step, which comprises one or more executable instructions for implementing the specified logical function (s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved.

The system and method of the embodiments can be embodied and/or implemented at least in part as a machine configured to receive a computer-readable medium storing computer-readable instructions. The instructions can be executed by computer-executable components integrated with an application, applet, host, server, network, website, communication service, communication interface, hardware/firmware/software elements of a user computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

A specific example of a uterine hemorrhage controlling system having features similar to those described herein is included below.

Figure 13:
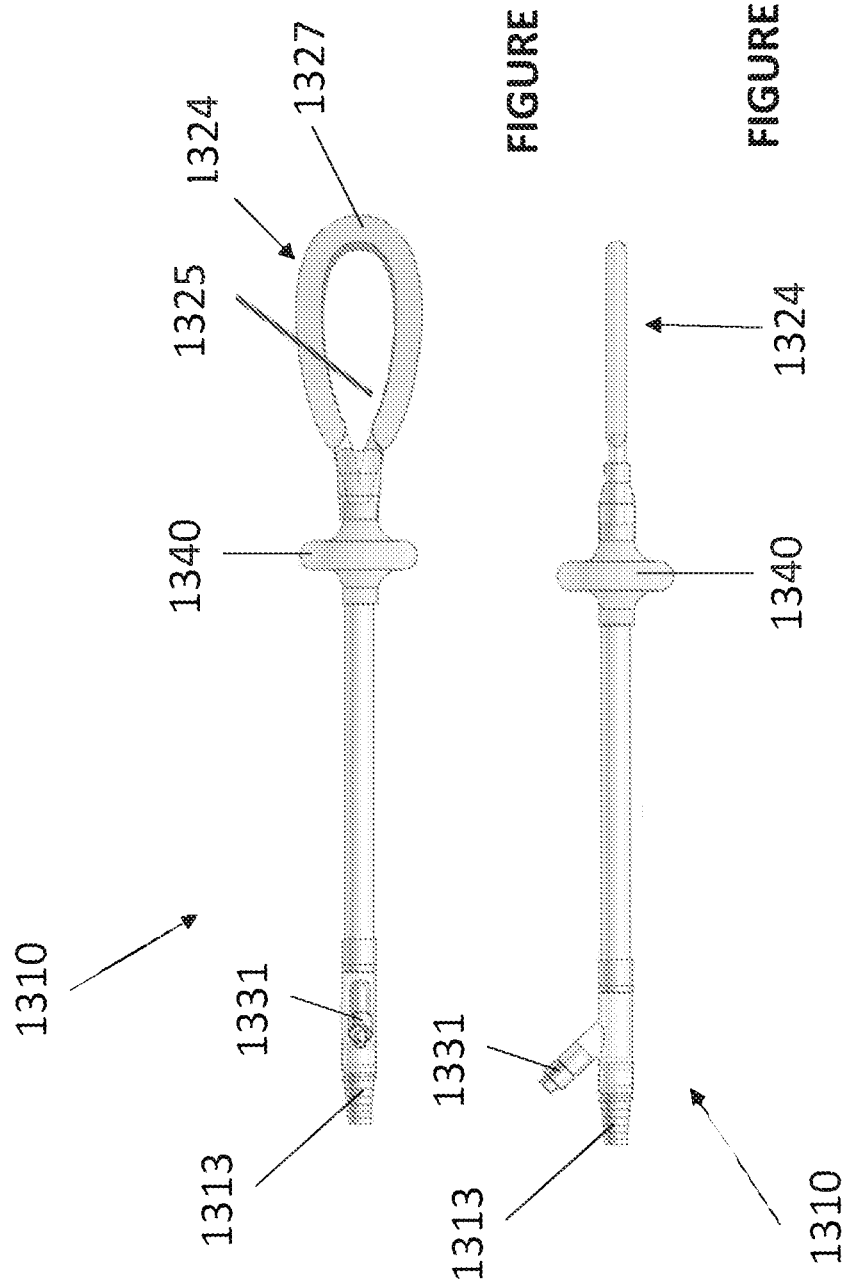
FIG. 13A is depicts an embodiment of a uterine hemorrhage controlling system.
FIG. 13B depicts the uterine hemorrhage controlling system of FIG. 13A viewed from the side.

Referring to FIGS. 13A-13B, a uterine hemorrhage controlling system for control and treatment of abnormal postpartum uterine bleeding or hemorrhage can include a suction module 1310. The suction module 1310 can be 41 cm long and made of silicone. Further, the suction module 1310 can include a curved intrauterine suction loop 1324 at the distal end of the suction module 1310. The flat curved suction loop 1324 can advantageously help ensure that the device is not expelled from the uterus during use. Further, the suction loop 1324 can include a plurality of openings 1325 (e.g., 20 openings 1325) oriented towards the inside diameter of the suction loop 1324. The outer surface of the suction loop 1324 can be covered by a shield 1327 that overhangs the openings 1325 to protect tissue from vacuum and the openings 1325 from plugging with tissue and blood clots. The suction loop 1324 and shield 1327 can advantageously be atraumatic and configured to collapse and/or deform before exerting any forces at the distal tip of the loop 1324. Further, the proximal end of the suction module 1310 can include a connecting tube 1326 between the loop 1324 and a vacuum connector 1313 for connection to sterile vacuum tubing. The sealing module 1340 can be filled and emptied with a syringe (e.g., a tapered and/or luer syringe) through the seal valve 1331.

The suction module 1310 (and corresponding system) can be used in patients experiencing atony or postpartum hemorrhaging. In some embodiments, the suction module 1310 can be used to treat patients who deliver at over 24 weeks or have a uterus greater than 24 weeks in size, who do not have an ongoing intrauterine pregnancy, who do not have an untreated uterine rupture, who do not have an unresolved uterine inversion, and/or who do not have cervical cancer.

An exemplary method of using the uterine hemorrhage controlling system with suction module 1310 is described below:

1. Evaluate for lacerations, retained products of conception, or other causes of bleeding prior to using the device.
2. Ensure that the bladder is empty in order to facilitate palpation and contraction of the uterus.
3. Connect a vacuum canister and sterile standard vacuum tubing to a regulated vacuum source.
4. Use a syringe (e.g., a tapered and/or luer syringe) to remove any air that is in the sealing module 1340. Ensuring that the sealing module 1340 is depleted of air prior to inserting the suction module 1310 can minimize the risk of air embolism should the sealing module leak and/or burst.
5. Fill the sterile syringe with 60 mL of sterile fluid.
6. Secure visualization of the cervix to confirm it is dilated ≥3 cm to allow for placement of the suction module 1310.
7. Grasp and compress the suction loop 1324 near the distal tip for support and insert the suction module 1310 transvaginally, leading with the suction loop 1324. Use gentle traction on the anterior cervical lip to stabilize the cervical opening, if needed.
8. Place the suction module 1310 such that the suction loop 1324 is located in the uterus and is oriented in the frontal or coronal plane of the body. In some embodiments, the fixed position of the valve seal 1331 relative to the suction loop 1324 can be used by the practitioner to determine the orientation of the suction loop 1324 (e.g., for the design shown in FIGS. 13A-13B, by assuring the seal valve 1331 is oriented at either 6 or 12 o'clock, i.e., perpendicular to the frontal plane).
9. After insertion, confirm that the suction loop 1324 is within the uterus while the sealing module 1340 is within the vagina at the external cervical os. Advantageously, this position enables vacuum distal to the sealing module 1340 and within the lower uterine segment (LUS) (in contrast to other mechanical means of treating PPH, such as the Bakri® balloon device, which cannot treat the LUS). Ultrasound may be used to confirm proper placement of the suction loop 1324 within the uterus. Because the suction loop 1324 is flat along one plane and curved along the opposite plane, the ultrasound can advantageously ensure that the loop 1324 is in the desired position.
10. In some cases, a B-Lynch compression suture may be used in conjunction with the sealing module 1340.
11. While securely holding the seal valve 1331 and avoiding unintentional proximal or distal movement of the sealing module 1340 away from the external cervical os, use the sterile syringe to fill the sealing module 1340 with 60 mL of sterile fluid. If needed, add up to another 60 mL of sterile fluid to achieve coverage of the external cervical os and create a seal for vacuum.
12. Set the vacuum source to 80 mm Hg+/−10 mm Hg while occluding the end of the tubing (80 mm Hg=1.5 psi=10.7 kPa=3.2 in Hg=106.7 mbar).
13. After the vacuum pressure has been set and confirmed, connect the suction module 1310 to the sterile vacuum tubing. Blood flow into the vacuum tubing and/or improvement in uterine tone should be noted after initiation of vacuum.
14. The position of the sealing module 1340 at the external cervical os can be confirmed after the suction module 1310 is in place. If necessary, the suction module 1310 can be repositioned to facilitate a seal. The presence of intermittent or continuous air flow through suction module 1310 and/or the connecting tube may indicate an issue with the location or inflation of the sealing module 1340 and can be used to adjust the location or inflation of the module 1340.
15. After initial evacuation of any pooled blood, presentation may vary during treatment: there may be no further blood evacuation, or additional blood moving into the tubing, or accumulation of blood in the canister. If blood flow does not stop or slow sufficiently, consider increasing the vacuum pressure.
16. Tape suction module 1310 to the patient's inner thigh without tension to avoid unintentional dislodgement.
17. Leave suction module 1310 in place with the vacuum applied until: (1) PPH/abnormal postpartum uterine bleeding is controlled for at least 1 hour, (2) the uterus is firm, and/or (3) the patient is stable.
18. Advantageously, repair of vaginal and external genital lacerations can be performed with the suction module 1310 in place because the sealing module 1340 blocks the flow of blood from the uterus. The provider can therefore determine if blood originates outside of the sealed volume and, if so, can repair the vaginal and external genital lacerations without obstruction of the view from blood stemming from the uterus. The sealing module 1340 can allow for confirmation that any repair that is done in the vagina with the sealing module 1340 in place has been a success. Conversely, the lack of bleeding from the vagina when the sealing module 1340 is in place can confirm that there are no lacerations in the vagina in need of repair.
19. Before disconnecting vacuum, assess the patient to confirm that treatment is no longer needed.
20. Disconnect vacuum tubing from the suction module 1310 while vacuum is on to collect any blood from the tubing into the canister. Secure tubing in case re-application of vacuum is needed.
21. Using a syringe (e.g., tapered and/or luer syringe), remove the fluid from the sealing module 1340 and keep the suction module 1310 in place for at least 30 minutes while monitoring for any recurrent uterine bleeding.
22. If PPH/abnormal postpartum uterine bleeding remains controlled and the uterus remains firm for at least 30 minutes after vacuum is disconnected, remove the suction module 1310 from the patient. To do so, place one hand on the abdomen to secure the uterine fundus while the other hand slowly withdraws the device.

A single-arm, literature-controlled, multi-center treatment study was performed where each enrolled subject was treated with a uterine hemorrhage controlling system including suction module 1310. The primary endpoint of the study was control of postpartum hemorrhage, defined as the avoidance of non-surgical, second line or surgical intervention to control uterine hemorrhage after the use of the suction module 1310 as described herein. During the study, the following features were evaluated: (1) time to hemorrhage control; (2) rate of non-surgical intervention required to control PPH after use; (3) rate of surgical intervention required to control PPH after use; (4) assessment of device usability; and (5) rate of blood product transfusion required after device use, and number of transfusion units when administered.

The comparator to the system with suction module 1310 was a literature meta-analysis of the Bakri® Postpartum Balloon. Based on a random effects model used in the meta-analysis, the estimated pooled proportion of subjects who reached control of uterine hemorrhage following Bakri® Postpartum Balloon treatments was 82.0% (95% CI: 73.4% to 89.2%). By this definition, the study was considered a success if the lower bound of the two-sided Exact Clopper-Pearson mid-p 95% Confidence Interval for the Study Treatment Success was greater than or equal to 73.4%.

A total of 107 subjects were enrolled in the study at 12 investigational centers in the United States, as shown below in Table 1.

TABLE 1

Subjects in Study

| Cohort | Subjects (N) |
|---|---|
| Total Subjects Enrolled* | 107 |
| Safety/Intent to Treat (ITT)** | 106 |
| Modified Intent to Treat (mITT)*** | 104 |
| Per Protocol (PP)**** | 97 |

In Table 1, * indicates all subjects in whom device insertion was attempted,  indicates all subjects in whom treatment was attempted with device (device inserted and vacuum turned on), * indicates all subjects in whom treatment was attempted with suction module 1310 (device inserted and vacuum turned on) and whose treatment was not aborted early for non-device reasons, and **** indicates all subjects who completed treatment according to the methods described herein, and who completed their 6-week visit without any major protocol or method deviations.

Figure 14:
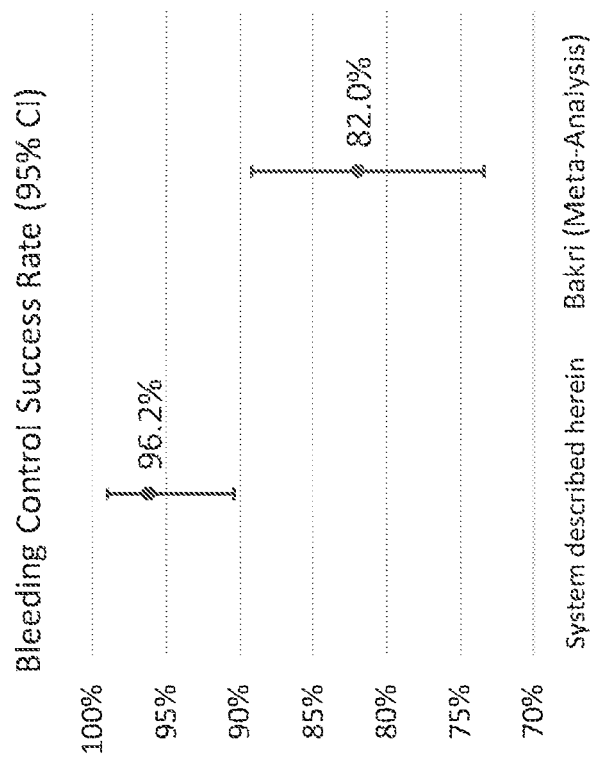
FIG. 14 is a graph comparing the bleeding control success rate of the uterine hemorrhage controlling system described herein relative to a Bakri device.

Referring to Table 2 and FIG. 14, the analysis of effectiveness was based on the 104 subjects in the mITT Cohort. The 97 subjects in the PP Cohort are also presented. The treatment success rate in the ITT Cohort was 94.3% (100/106, p<0.001), with a lower bound 95% confidence limit of 88.1%. The treatment success rate of the comparator, Bakri Postpartum Balloon, was 82.0% (95% CI: 73.4% to 89.2%). The treatment success rate in the mITT Cohort is 96.2 (95% CI: 90.4%, 98.9%). The results demonstrate that in the mITT cohort the confidence intervals do not overlap with the Bakri Postpartum Balloon comparator.

TABLE 2

Primary Effectiveness

| Cohort (N) | Treatment Success | 95% Confidence Limit (2-sided) | P value |
|---|---|---|---|
| ITT (N = 106) | 94.3% (100/106) | 88.1%, 97.9% | <0.001 |
| mITT (N = 104) | 96.2% (100/104) | 90.4%, 98.9% | <0.001 |
| PP (N = 97) | 99.0% (96/97) | 94.4%, 100% | <0.001 |

Control of hemorrhage was defined in the study as the time from connecting the vacuum source to the suction module 1310 to the time the first of any of the following occurs: there is no blood being collected in the tubing or canister, or the blood loss is observed as leveled off in the canister, or blood loss is at a rate of <500 mL in 24 hours. The median time to control of PPH in both the mITT and PP population was 3 minutes.

Referring to Table 3, timing of the procedure and duration of treatment was tracked from diagnosis through treatment and patient discharge for subjects enrolled in the study. The suction module 1310 was used most often within one hour after delivery. Bleeding was controlled quickly from the time of connection of vacuum, with a median control in three minutes. The duration of treatment with active vacuum connected was a median of 2 hours and 24 minutes with total in-dwelling time median of 3 hours and 11 minutes.

TABLE 3

Duration of Treatment
Duration of Treatment (ITT Cohort (N = 106*))

| | Time (minutes) | | | |
|---|---|---|---|---|
| Procedural Steps | Mean | SD | Median | Min, Max |
| Time to control of hemorrhage | 4.2 | 5.3 | 3.0 | 0, 35.0 |
| Duration of Vacuum Treatment (Protocol: ≥60 minutes) | 248.8 | 261.1 | 144.0 | 57, 1276 |
| Total in-dwelling time (Treatment + Verification) | 306.0 | 274.9 | 191.0 | 70, 1400 |

*Timing of steps was available in 100 subjects in whom bleeding was successfully controlled with device alone.

The median hospital length of stay from delivery time was 2.2 days.

As shown in Table 4, the need for non-surgical intervention after use of the suction module 1310 was rare, with only 2 subjects receiving non-surgical intervention in the mITT Cohort. Surgical intervention after treatment with the suction module 1310 was reported in three subjects: one subject received a B-Lynch compression suture in conjunction with the device, one subject received B-Lynch compression suture followed by hysterectomy, and one subject underwent hysterectomy.

TABLE 4

Rate of Non-Surgical and Surgical Intervention after Use

| Cohort | Non-Surgical Intervention | Surgical Intervention | No Intervention Needed |
|---|---|---|---|
| ITT | 2/106 (1.9%) (95% CI: 0.2%, 6.7%) | 3/106 (2.8%) (95% CI: 0.6%, 8.1%) | 101/106 (95.3%) |
| mITT | 1/104 (0.9%) (95% CI: 0%, 5.2%) | 3/104 (2.9%) (95% CI: 0.6%, 8.2%) | 100/104 (96.2%) |
| PP | 0/97 (0%) | 1/97 (1.0%) | 96/97 (99%) |

Referring to Table 5, the device usability was notably positive by investigators on all measurements.

TABLE 5

Investigator Feedback
Investigators' Experience with Use (Enrollment Cohort (N = 107))

| Category Evaluated | Response (Agreed or Strongly Agreed) |
|---|---|
| IFU and device training clearly explained use | 100% |
| Device was easy to insert and position | 96.3% |
| Device was easy to remove | 98.1% |
| Device use did not inhibit other care | 98.1% |
| Device was easy to use | 98.1% |
| Would recommend Device to treat PPH | 97.2% |

In the study, 40 subjects (37.7%) in the ITT Cohort, 38 subjects (36.5%) in the mITT Cohort, and 33 subjects (34.0%) in the PP Cohort received any blood product replacement. Transfusion of four or more units of packed red blood cells (PRBC) occurred in five subjects (4.7%) in the ITT Cohort, five subjects (4.8%) in the mITT Cohort, and four subjects (4.1%) in the PP Cohort. No subject developed disseminated intravascular coagulation (DIC) on the study.

As shown in Table 6, sub-group analysis of effectiveness rate was evaluated by mode of delivery, vaginal or c-section. For the ITT population of 106 subjects, there were 91 vaginal deliveries with three failures, and 15 c-sections with three failures. The success rates in the ITT Cohort were 96.7% and 80.0% after vaginal and c-section birth, respectively. In the mITT Cohort, success rates were 98.9% and 80.0%, respectively. In the PP Cohort, the success rates were 100.0% and 91.7%, respectively.

TABLE 6

Effectiveness by Delivery Type/Cohort

| | Vaginal Delivery | | | C-Section | | |
|---|---|---|---|---|---|---|
| Primary Effectiveness | ITT (N = 91) | mITT (N = 89) | PP (N = 85) | ITT (N = 15) | mITT (N = 15) | PP (N = 12) |
| | 88/91 (96.7%) | 88/89 (98.9%) | 85/85 (100.0%) | 12/15 (80.0%) | 12/15 (80.0%) | 11/12 (91.7%) |
| Time to Hemorrhage Control with Device Success (minutes) | ITT (N = 88) | mITT (N = 88) | PP (N = 85) | ITT (N = 12) | mITT (N = 12) | PP (N = 11) |
| Mean | 3.8 | 3.8 | 3.8 | 7.1 | 7.1 | 7.2 |
| SD | 4.6 | 4.6 | 4.6 | 8.7 | 8.7 | 9.1 |
| Median | 3.0 | 3.0 | 3.0 | 4.0 | 4.0 | 3.0 |
| Min, Max | 0, 35 | 0, 35 | 0, 35 | 0, 29 | 0, 29 | 0, 29 |

The results of the study demonstrated that the system described herein (e.g., with module 1310) is safe with an effectiveness rate of 94.3% for its intended use. The effectiveness rates in the mITT and PP Cohorts were 96.2% and 99.0%, respectively. There were no adverse events judged definitely related to the device or the procedure, and there was a low rate of possibly related adverse events, all of which were anticipated in this patient population and with introduction of an intrauterine device.

The secondary endpoints were also overwhelmingly positive. Bleeding was controlled in 3 minutes in both the mITT and PP populations. The rate of further surgical or non-surgical intervention after use was very low. The rate of blood transfusion was expected in this patient population, treated at U.S. hospitals with ready access to these resources. The median reported total time for treatment with vacuum in the study was 2 hours and 24 minutes, and total in-dwelling time was 3 hours and 11 minutes.

It should be understood that any feature described herein with respect to one embodiment can be used in addition to or in place of any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

As a person skilled in the art will recognize from the previous detailed description and from the figures and claims, modifications and changes can be made to the preferred embodiments of the invention without departing from the scope of this invention defined in the following claims.

We claim:

1. A method of reducing postpartum bleeding, comprising:
   positioning a device comprising a vacuum element and a sealing element, the vacuum element having a plurality of openings along a circumference thereof and distal to the sealing element such that the sealing element is located within the vaginal canal and the plurality of openings is located within the uterine cavity distal to the vaginal canal;
   sealing the uterus with the sealing element;
   activating vacuum in the uterine cavity through the openings while the uterine cavity is sealed; and
   collapsing the uterine cavity with the vacuum to reduce postpartum bleeding, wherein collapsing the uterus comprises collapsing uterine walls onto a shield of the device so as to prevent obstruction of the plurality of openings.

2. The method of claim 1, wherein positioning the device comprises transvaginally delivering the vacuum element into the uterus.

3. The method of claim 1, wherein sealing the uterus comprises placing a seal at the vulva, cervix, or vaginal canal.

4. The method of claim 1, wherein sealing the uterus comprises expanding a seal against tissue proximate to or within the uterus.

5. The method of claim 4, wherein expanding the seal comprises delivering fluid to an interior of the seal.

6. The method of claim 1, wherein activating vacuum comprises activating vacuum with a vacuum pump connected to the vacuum element.

7. The method of claim 1, wherein activating vacuum comprises producing a negative pressure within the uterus of up to 3 psi.

8. The method of claim 1, further comprising removing fluid from the uterus after activating vacuum.

9. The method of claim 1, wherein the step of activating vacuum includes activating vacuum so as to counteract uterine atony.

10. The method of claim 1, wherein the step of activating vacuum includes activating vacuum so as to facilitate closing of exposed uterine arterioles in a wall of the uterus.

11. The method of claim 1, further comprising maintaining vacuum until hemorrhaging has substantially stopped.

12. The method of claim 1, further comprising maintaining vacuum for 1-24 hours.

13. The method of claim 1, further comprising monitoring a flow of blood out of the uterus while vacuum is activated.

14. The method of claim 13, wherein monitoring the flow of blood comprises monitoring through a transparent portion of the device.

15. The method of claim 1, wherein positioning the device at least partially within the uterus comprises positioning at least one opening of the vacuum element within the uterus.

16. A method of reducing postpartum bleeding, comprising:
- positioning a device comprising a curved loop vacuum element and a sealing element, the curved loop vacuum element having a plurality of openings positioned along an inner circumference thereof and distal to the sealing element such that the sealing element is located within the vaginal canal and the plurality of openings is located within the uterine cavity distal to the vaginal canal;
- sealing the uterus with the sealing element;
- activating vacuum in the uterine cavity through the openings of the curved loop vacuum element while the uterine cavity is sealed; and
- collapsing the uterine cavity with the vacuum to reduce postpartum bleeding wherein collapsing the uterus comprises collapsing uterine walls onto an outer circumference of the curved loop vacuum element so as to prevent obstruction of the plurality of openings.

17. The method of claim 16, further comprising reversibly deforming the curved loop vacuum element prior to positioning the curved loop vacuum element within the uterus.

18. A method of reducing postpartum bleeding, comprising:
- transvaginally delivering a device into a uterus, the device comprising a set of suction tubes and a sealing element, the set of suction tubes including an outer suction tube having a curved loop portion with plurality of openings positioned along an inner circumference thereof and an inner suction tube having a shorter length than the outer suction tube and having a curved looped portion that is within the outer suction tube, and the set of suction tubes located distal to the sealing element such that the sealing element is located within the vaginal canal and the plurality of openings is located within the uterine cavity distal to the vaginal canal;
- sealing the uterus with the sealing element;
- transmitting, via the set of suction tubes, a negative pressure to an interior of the uterine cavity while the uterine cavity is sealed; and
- collapsing the uterine cavity with the negative pressure wherein collapsing the uterus comprises collapsing uterine walls onto the outer suction tube so as to prevent obstruction of the plurality of openings.

* * * * *